(12) United States Patent
Gallant et al.

(10) Patent No.: US 8,499,503 B2
(45) Date of Patent: Aug. 6, 2013

(54) THERMOREGULATION EQUIPMENT FOR PATIENT ROOM

(75) Inventors: Dennis J. Gallant, Harrison, OH (US);
Dennis M. Lanci, Carlsbad, CA (US);
John P. Biondo, Durant, IA (US)

(73) Assignee: Hill-Rom Services, Inc., Batesville, IN (US)

(*) Notice: Subject to any disclaimer, the term of this patent is extended or adjusted under 35 U.S.C. 154(b) by 234 days.

(21) Appl. No.: 12/773,415

(22) Filed: May 4, 2010

(65) Prior Publication Data

US 2010/0205739 A1 Aug. 19, 2010

Related U.S. Application Data

(60) Continuation of application No. 12/135,244, filed on Jun. 9, 2008, now Pat. No. 7,735,266, which is a continuation of application No. 11/605,018, filed on Nov. 28, 2006, now Pat. No. 7,392,621, which is a continuation of application No. 10/885,369, filed on Jul. 6, 2004, now Pat. No. 7,219,472, which is a division of application No. 10/154,314, filed on May 23, 2002, now Pat. No. 7,040,057.

(60) Provisional application No. 60/293,949, filed on May 25, 2001.

(51) Int. Cl.
*E04B 2/74* (2006.01)

(52) U.S. Cl.
USPC ............... 52/36.5; 52/27; 52/36.1; 607/104; 5/421

(58) Field of Classification Search
USPC .... 52/34.2, 36.2, 28, 27, 36.1, 36.5; 607/104, 607/107; 5/421, 423
See application file for complete search history.

(56) References Cited

U.S. PATENT DOCUMENTS

| 750,179 A | 1/1904 | Foglesong |
| 1,110,494 A | 9/1914 | Kellogg |
| 1,121,277 A | 12/1914 | Mitchell |
| 1,399,095 A | 12/1921 | Webb |
| 2,250,325 A | 7/1941 | Barnes |

(Continued)

FOREIGN PATENT DOCUMENTS

| EP | 0 542 383 | 5/1993 |
| EP | 0 757 907 A1 | 2/1997 |
| EP | 0 821 928 A2 | 7/1998 |
| WO | WO 02/29348 | 4/2002 |

OTHER PUBLICATIONS

Gorix Electro-conductive Textiles, http://www.gorix.com/gorix/GOIX.HTM (accessed Jun. 24, 1999).

(Continued)

*Primary Examiner* — Joshua J Michener
*Assistant Examiner* — Chi Q Nguyen
(74) *Attorney, Agent, or Firm* — Barnes & Thornburg LLP

(57) ABSTRACT

An architectural system adaptable to patient acuity level has a headwall unit with a cavity, a ceiling unit, and a column coupled to the ceiling unit. The column is movable between a first position in which at least a majority of the column is situated in the cavity and a second position in which the column is situated outside the cavity. Various types of patient-care equipment is also disclosed. The patient-care equipment is included in, or is coupleable to, one or more of the ceiling unit, the headwall unit, or the column.

17 Claims, 18 Drawing Sheets

U.S. PATENT DOCUMENTS

| | | | | |
|---|---|---|---|---|
| 2,272,481 A | | 2/1942 | Rinkes et al. | |
| RE22,763 E | | 6/1946 | Clark | |
| 2,415,455 A | | 2/1947 | Barnes et al. | |
| 2,582,648 A | | 1/1952 | Mowbray | |
| 2,606,996 A | | 8/1952 | Westerberg et al. | |
| 2,792,827 A | | 5/1957 | Gravin et al. | |
| 2,832,336 A | | 4/1958 | Davis et al. | |
| 2,932,491 A | | 4/1960 | Miller | |
| 3,094,983 A | | 6/1963 | MacLeod | |
| 3,186,404 A | | 6/1965 | Gardner | |
| 3,295,594 A | | 1/1967 | Hopper | |
| 3,714,947 A | | 2/1973 | Hardy | |
| 3,757,366 A | * | 9/1973 | Sacher | 5/423 |
| 3,785,374 A | | 1/1974 | Lipson | |
| 3,789,853 A | | 2/1974 | Reinhard | |
| 3,808,403 A | | 4/1974 | Kanaya et al. | |
| 3,854,156 A | | 12/1974 | Williams | |
| 3,869,594 A | | 3/1975 | Shively | |
| 3,918,458 A | | 11/1975 | Nethery | |
| 3,967,627 A | | 7/1976 | Brown | |
| 3,993,053 A | | 11/1976 | Grossan | |
| 4,013,069 A | | 3/1977 | Hasty | |
| 4,029,087 A | | 6/1977 | Dye et al. | |
| 4,113,222 A | * | 9/1978 | Frinzel | 248/412 |
| 4,114,620 A | | 9/1978 | Moore et al. | |
| 4,149,529 A | | 4/1979 | Copeland et al. | |
| 4,149,541 A | | 4/1979 | Gammons et al. | |
| 4,156,425 A | | 5/1979 | Arkans | |
| 4,168,063 A | | 9/1979 | Rowland | |
| 4,198,961 A | | 4/1980 | Arkans | |
| 4,207,875 A | | 6/1980 | Arkans | |
| 4,207,876 A | | 6/1980 | Annis | |
| 4,253,449 A | | 3/1981 | Arkans et al. | |
| 4,265,789 A | | 5/1981 | Christopherson et al. | |
| 4,280,485 A | | 7/1981 | Arkans | |
| 4,281,647 A | | 8/1981 | Antypas | |
| 4,320,746 A | | 3/1982 | Arkans et al. | |
| 4,331,133 A | | 5/1982 | Arkans | |
| 4,335,726 A | | 6/1982 | Kolstedt | |
| 4,338,944 A | | 7/1982 | Arkans | |
| 4,370,975 A | | 2/1983 | Wright | |
| 4,372,297 A | | 2/1983 | Perlin | |
| 4,375,217 A | | 3/1983 | Arkans | |
| 4,396,010 A | | 8/1983 | Arkans | |
| 4,402,312 A | | 9/1983 | Villari et al. | |
| 4,423,308 A | | 12/1983 | Callaway et al. | |
| 4,476,867 A | | 10/1984 | Parks | |
| 4,481,937 A | | 11/1984 | Arkans | |
| 4,523,594 A | | 6/1985 | Kuznetz | |
| 4,574,812 A | | 3/1986 | Arkans | |
| 4,638,392 A | | 1/1987 | Cartier et al. | |
| 4,668,857 A | | 5/1987 | Smuckler | |
| 4,747,409 A | | 5/1988 | Silen | |
| 4,773,397 A | | 9/1988 | Wright et al. | |
| 4,787,104 A | * | 11/1988 | Grantham | 5/613 |
| 4,857,384 A | | 8/1989 | Mio et al. | |
| 4,858,596 A | | 8/1989 | Kolstedt et al. | |
| 4,938,208 A | | 7/1990 | Dye | |
| 5,007,411 A | | 4/1991 | Dye | |
| 5,031,604 A | | 7/1991 | Dye | |
| 5,034,006 A | | 7/1991 | Hosoda et al. | |
| 5,051,673 A | | 9/1991 | Goodwin | |
| 5,074,285 A | | 12/1991 | Wright | |
| 5,117,812 A | | 6/1992 | McWhorter | |
| 5,165,127 A | * | 11/1992 | Nicholson | 5/421 |
| 5,169,384 A | | 12/1992 | Bosniak et al. | |
| 5,186,163 A | | 2/1993 | Dye | |
| 5,251,347 A | | 10/1993 | Hopper et al. | |
| 5,263,473 A | | 11/1993 | McWhorter | |
| 5,300,101 A | | 4/1994 | Augustine et al. | |
| 5,304,213 A | * | 4/1994 | Berke et al. | 607/104 |
| 5,320,164 A | | 6/1994 | Szczesuil et al. | |
| 5,324,320 A | | 6/1994 | Augustine et al. | |
| 5,336,250 A | | 8/1994 | Augustine | |
| 5,342,285 A | | 8/1994 | Dye | |
| 5,350,417 A | | 9/1994 | Augustine | |
| 5,369,807 A | | 12/1994 | Cho et al. | |
| 5,370,674 A | | 12/1994 | Farrell | |
| 5,373,595 A | | 12/1994 | Johnson et al. | |
| 5,396,373 A | * | 3/1995 | Mori et al. | 360/22 |
| 5,402,542 A | | 4/1995 | Viard | |
| 5,415,618 A | | 5/1995 | Koch | |
| 5,415,934 A | | 5/1995 | Mori | |
| 5,444,878 A | | 8/1995 | Kang | |
| 5,449,379 A | | 9/1995 | Hadtke | |
| 5,455,975 A | * | 10/1995 | Foster | 5/600 |
| 5,522,871 A | | 6/1996 | Sternlicht | |
| 5,542,136 A | | 8/1996 | Tappel | |
| 5,590,648 A | * | 1/1997 | Mitchell et al. | 600/301 |
| 5,609,619 A | | 3/1997 | Pompei | |
| 5,626,556 A | | 5/1997 | Tobler et al. | |
| 5,642,539 A | * | 7/1997 | Kuo | 5/423 |
| 5,647,079 A | | 7/1997 | Hakamiun et al. | |
| 5,658,325 A | | 8/1997 | Augustine | |
| 5,683,438 A | | 11/1997 | Grahn | |
| 5,683,441 A | | 11/1997 | Dickerhoff et al. | |
| 5,773,275 A | | 6/1998 | Anderson et al. | |
| 5,795,312 A | | 8/1998 | Dye | |
| 5,817,147 A | * | 10/1998 | Wolf | 607/104 |
| 5,871,526 A | | 2/1999 | Gibbs et al. | |
| 5,913,886 A | | 6/1999 | Soloman | |
| 5,941,907 A | * | 8/1999 | Augustine | 607/104 |
| 5,948,303 A | | 9/1999 | Larson | |
| 5,957,830 A | | 9/1999 | Skulic | |
| 5,970,550 A | | 10/1999 | Gazes | |
| 5,991,948 A | * | 11/1999 | Stanley et al. | 5/709 |
| 6,010,528 A | | 1/2000 | Augustine et al. | |
| 6,033,432 A | | 3/2000 | Augustine et al. | |
| 6,036,722 A | | 3/2000 | Augustine | |
| 6,049,927 A | | 4/2000 | Thomas et al. | |
| 6,073,284 A | | 6/2000 | Borders | |
| 6,078,026 A | | 6/2000 | West | |
| 6,128,796 A | | 10/2000 | McCormick et al. | |
| 6,138,676 A | | 10/2000 | Bruhn | |
| 6,148,457 A | * | 11/2000 | Sul | 5/421 |
| 6,149,674 A | | 11/2000 | Borders | |
| 6,156,058 A | | 12/2000 | Kappel et al. | |
| 6,182,315 B1 | | 2/2001 | Lee | |
| 6,565,699 B1 | | 5/2003 | Szczesuil et al. | |
| 6,582,456 B1 | | 6/2003 | Hand et al. | |
| 6,585,709 B2 | * | 7/2003 | Maimets | 604/355 |
| 6,800,087 B2 | * | 10/2004 | Papay et al. | 607/104 |
| 6,942,015 B1 | | 9/2005 | Jenkins | |
| 7,735,266 B2 | * | 6/2010 | Gallant et al. | 52/36.4 |
| 2003/0079488 A1 | | 5/2003 | Bieberich | |
| 2010/0057169 A1 | | 3/2010 | King et al. | |

OTHER PUBLICATIONS

Heated Beds, http://www.gorix.com/gorix/BEDS.HTM (accessed Jun. 24, 1999).

Electro-conductive Textiles??, http://www.gorix.com/gorix/WHATARE.HTM (accessed Jun. 24, 1999).

* cited by examiner

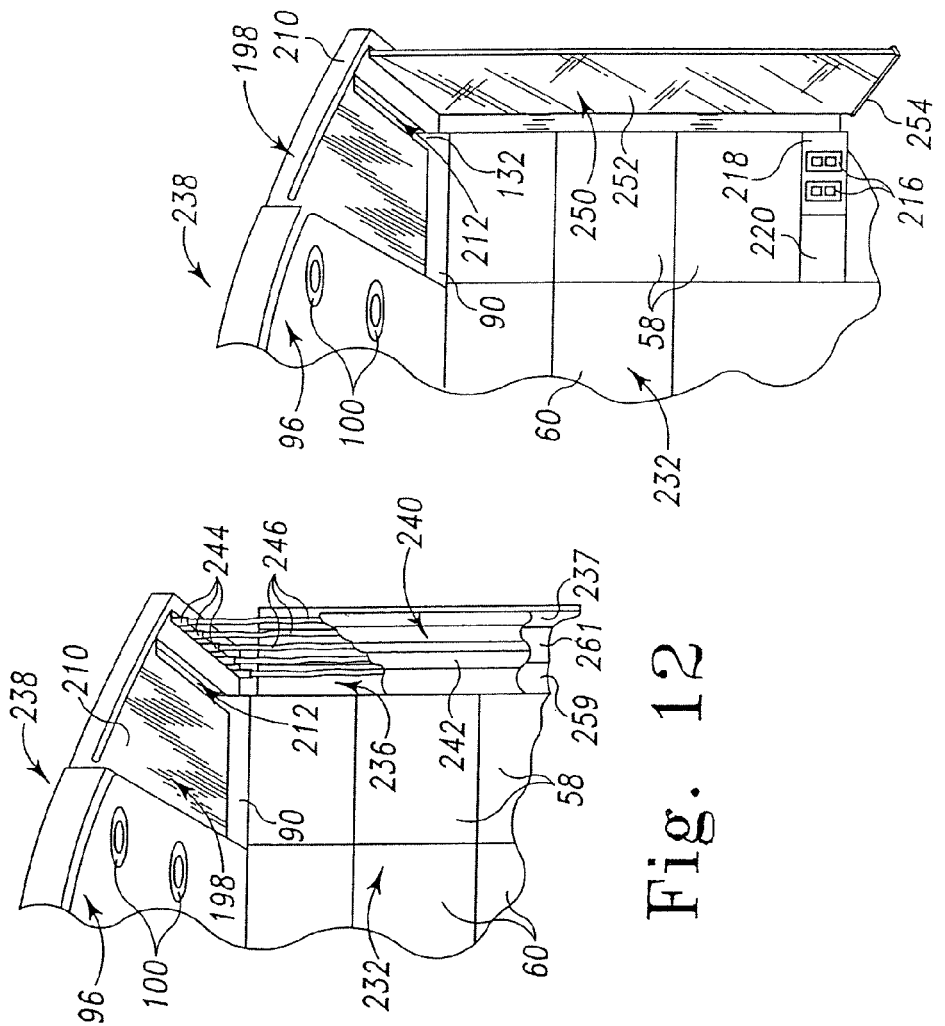
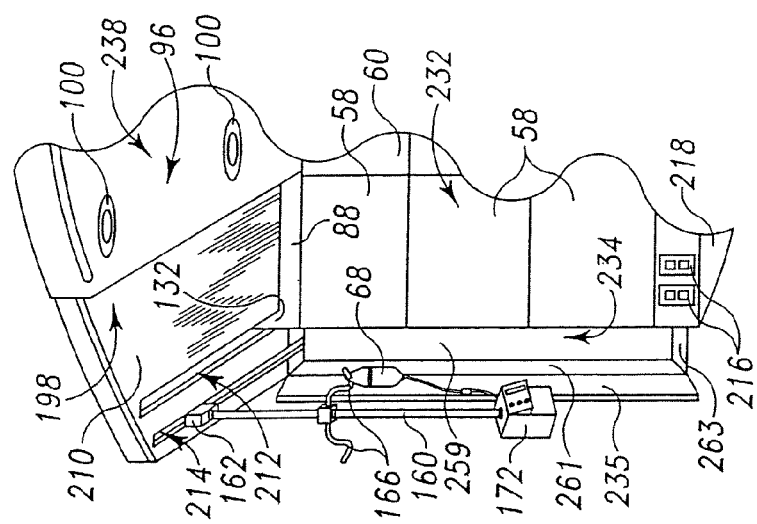

US 8,499,503 B2

THERMOREGULATION EQUIPMENT FOR PATIENT ROOM

CROSS REFERENCE TO RELATED APPLICATIONS

This application is a continuation of U.S. application Ser. No. 12/135,244, filed Jun. 9, 2008, now U.S. Pat. No. 7,735,266, which is a continuation of U.S. application Ser. No. 11/605,018, filed Nov. 28, 2006, now U.S. Pat. No. 7,392,621, which is a continuation of U.S. application Ser. No. 10/885,369, filed Jul. 6, 2004, now U.S. Pat. No. 7,219,472, which is hereby incorporated by reference herein, and which is a divisional application of U.S. application Ser. No. 10/154,314, filed May 23, 2002, now U.S. Pat. No. 7,040,057, which is hereby incorporated by reference herein, and which claimed priority under 35 U.S.C. §119(e) to U.S. Provisional Patent Application Ser. No. 60/293,949, filed on May 25, 2001, which is hereby incorporated by reference herein.

BACKGROUND AND SUMMARY

The present disclosure relates to architectural systems, such as headwalls, columns, and ceiling-suspended arm assemblies used in hospitals, and particularly to an architectural system adaptable to patient acuity level. More particularly, the present disclosure relates to an architectural system that is configured to deliver services, such as medical gases, to a patient and/or that is configured to support patient-care devices for delivering intensive care services to a patient.

Architectural systems, such as headwalls, columns, and ceiling-suspended arm assemblies, through which medical gases are accessible via medical service outlets are known. Headwalls, columns, and arm assemblies having rails, tracks, or brackets for attachment of patient-care devices and having electrical outlets for delivering power to the patient-care devices are also known. Patients in critical condition are oftentimes located in an intensive care unit of a hospital, whereas patients in stable condition are oftentimes located in a standard patient room. Architectural systems in intensive care units are generally configured to hold more patient-care devices and provide more types of medical services than architectural systems found in a standard patient room.

The numbers of patients in critical condition and the numbers of patients in stable condition fluctuate in a hospital over time. Thus, at any given time there may be either a shortage or excess of spaces for patients in an intensive care unit. In addition, at any given time there may be either a shortage or surplus of standard hospital rooms. Thus, there is a need for an architectural system that is adaptable to patients having high, medium, and low acuity levels so that hospitals have the flexibility to meet the needs of the patient population at any give time.

According to this disclosure, an architectural system adaptable to an acuity level of a patient supported by a hospital bed in a patient room having a wall and a ceiling is provided. The architectural system comprises a wall unit coupled to the wall and having a cavity, a ceiling unit coupled to the ceiling, and a column coupled to the ceiling unit for movement between a first position in which at least a majority of the column is situated in the cavity and a second position in which the column is situated outside the cavity.

Various patient-care devices and equipment are attachable to the column. Such patient care devices include, for example, IV racks, infusion pumps, ventilation equipment, heart rate monitoring equipment, and patient data acquisition equipment. In an illustrative embodiment, a number of medical service outlets, such as gas outlets and electrical outlets, are coupled to the column. Also in the illustrative embodiment, a number of doors are coupled to the wall unit for opening and closing the cavity. Thus, when the column is in the cavity, the doors may be moved to closed positions shielding the column and the equipment carried by the column from view and blocking access to the medical service outlets on the column. Opening the doors, but leaving the column in the cavity of the headwall unit, permits access to some of the medical service outlets and to some portions of the equipment carried by the column. When the column is moved out of the cavity, all of the medical service outlets and all pertinent portions of the equipment carried by the column are accessible.

Also according to this disclosure, a ceiling unit having one or more pieces of equipment coupled thereto is provided. Such equipment includes, for example, a reading light, an examination light, a display screen, air curtain generation equipment, a privacy curtain, a temperature sensor, an air quality sensor, an air purifier, aroma therapy equipment, a motion sensor, and a proximity sensor. In one illustrative embodiment, an arm assembly is coupled to the ceiling unit and supports an overbed table. The arm assembly permits the overbed table to be moved from one side of a hospital bed to an opposite side of the hospital bed.

A mobile cart is also disclosed herein. In an illustrative embodiment, the mobile cart comprises an upstanding pedestal, a plurality of legs coupled to a bottom of the upstanding pedestal, and a plurality of wheels. Each wheel is coupled to a respective leg of the plurality of legs. The legs, along with the wheels coupled thereto, are each movable between a first position extending outwardly from beneath the upstanding pedestal and a second position tucked beneath the upstanding pedestal. The mobile cart is attachable to a ceiling-mounted column or an arm assembly. The mobile cart is also attachable to a hospital bed to be transported with the bed. When the mobile cart is attached to either the column, the arm assembly, or the bed, the wheels of the mobile cart are spaced apart for the floor. A headwall unit having a cavity configured to receive the mobile cart is also disclosed. The mobile cart carries one or more pieces of patient-care equipment such as, for example, an IV pole, an infusion pump, a ventilator control unit, a gas tank, a gas control unit, a vital signs monitor, an on-board computer, a receiver, a transmitter, and a battery.

Further according to this disclosure, a set of hospital equipment comprises a headwall, a blanket, a unit housed in the headwall, and a hose coupled to the blanket and coupled to the unit, a thermoregulation medium being moved between the blanket and the unit through the hose. The thermoregulation medium includes, for example, heated air, cooled air, a heated liquid, or a cooled liquid. In some embodiments, in which the thermoregulation medium is heated or cooled air, the blanket has a plurality of perforations through which the heated or cooled air is expelled.

Additional features will become apparent to those skilled in the art upon consideration of the following detailed description of illustrative embodiments exemplifying the best mode of carrying out the various inventions disclosed herein as presently perceived.

BRIEF DESCRIPTION OF THE DRAWINGS

The detailed description particularly refers to the accompanying figures, in which:

FIG. 12 is a perspective view of a portion of the architectural system of FIG. 11 showing a privacy curtain moved out of an auxiliary cavity of the headwall unit and hanging from one of the lateral extensions of the ceiling unit;

FIG. 13 is a perspective view, similar to FIG. 12, showing an alternative embodiment of a privacy curtain extending downwardly from one of the lateral extensions of the ceiling unit;

FIG. 14 is a perspective view, similar to FIGS. 12 and 13, but of another portion of the architectural system of FIG. 11 showing an auxiliary IV pole moved out of an auxiliary compartment of the headwall unit and hanging from one of the lateral extensions of the ceiling unit;

DETAILED DESCRIPTION OF THE DRAWINGS

Figure 1:
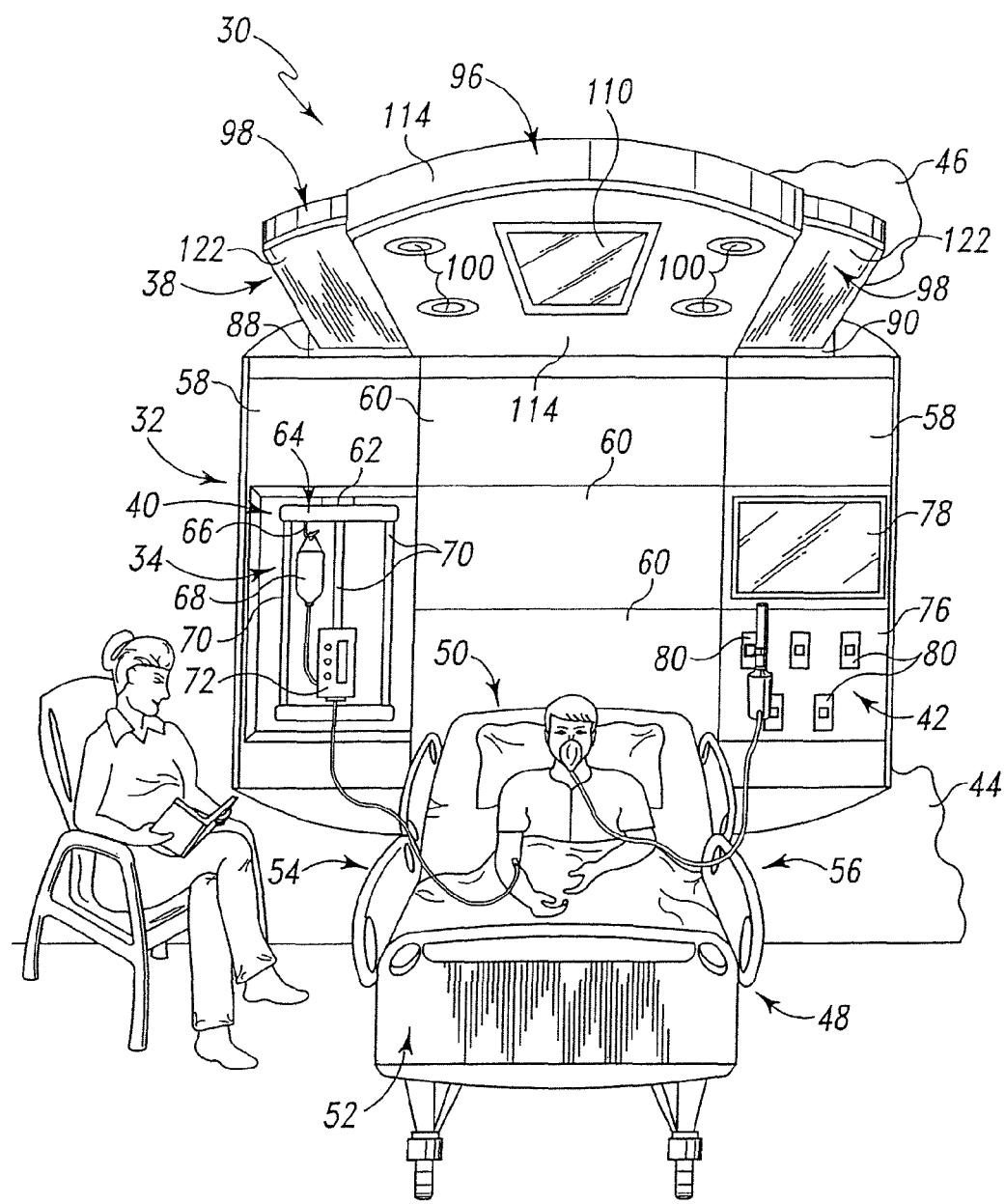
FIG. 1 is a perspective view of an architectural system adaptable to patient acuity level according to this disclosure showing a headwall unit behind a hospital bed on which a patient is resting, a ceiling unit extending from the headwall unit, the ceiling unit overlying the hospital bed, an IV rack situated in a first cavity of the headwall unit, and a housing having a display screen and a number of medical service outlets situated in a second cavity of the headwall unit.
Figure 2:
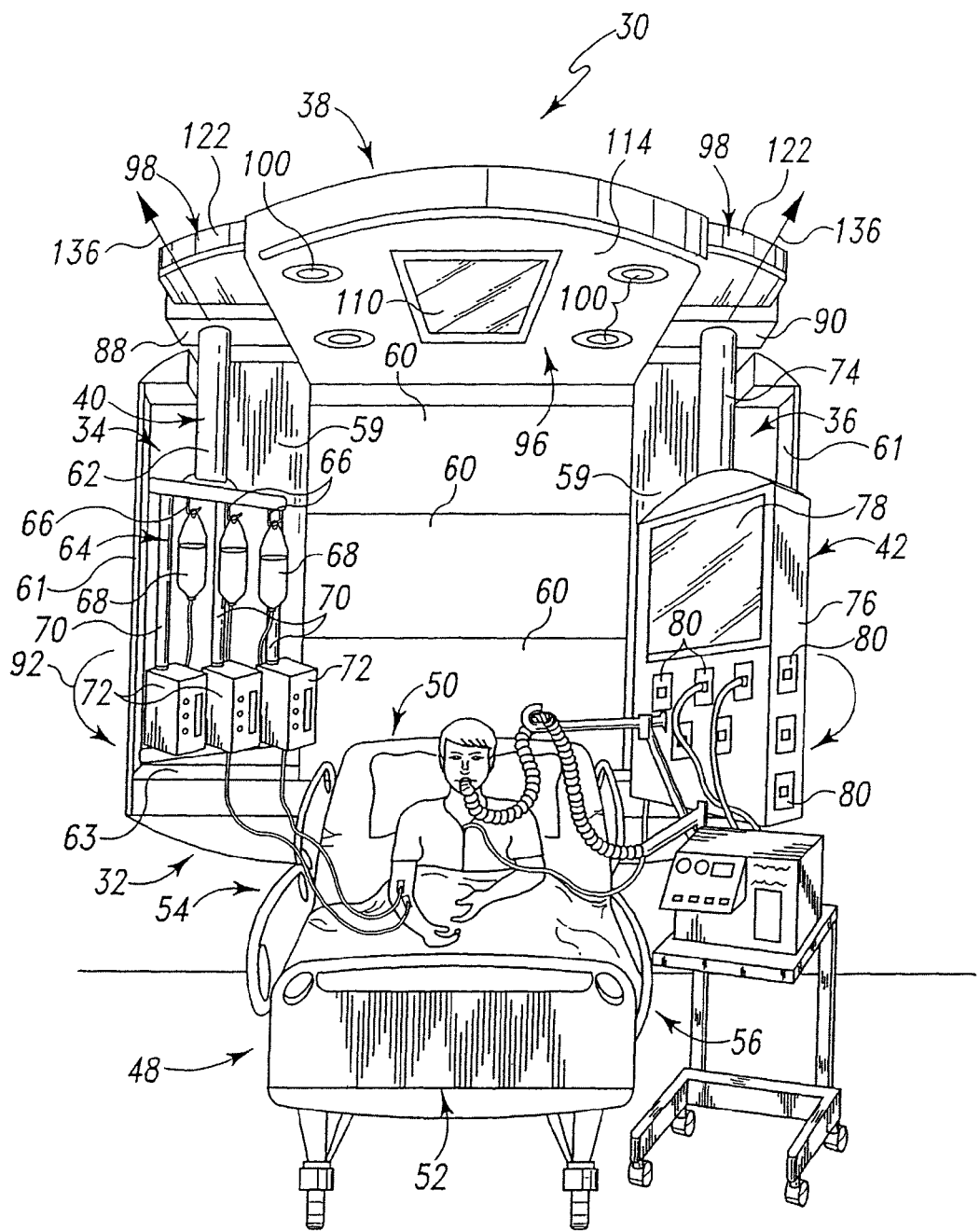
FIG. 2 is a perspective view, similar to FIG. 1, showing a first column moved out of first cavity so that the IV rack carried by the first column is situated alongside a first side of the hospital bed and a second column moved out of the second cavity so that the housing included as part of the second column is situated alongside a second side of the hospital bed.
Figure 4:
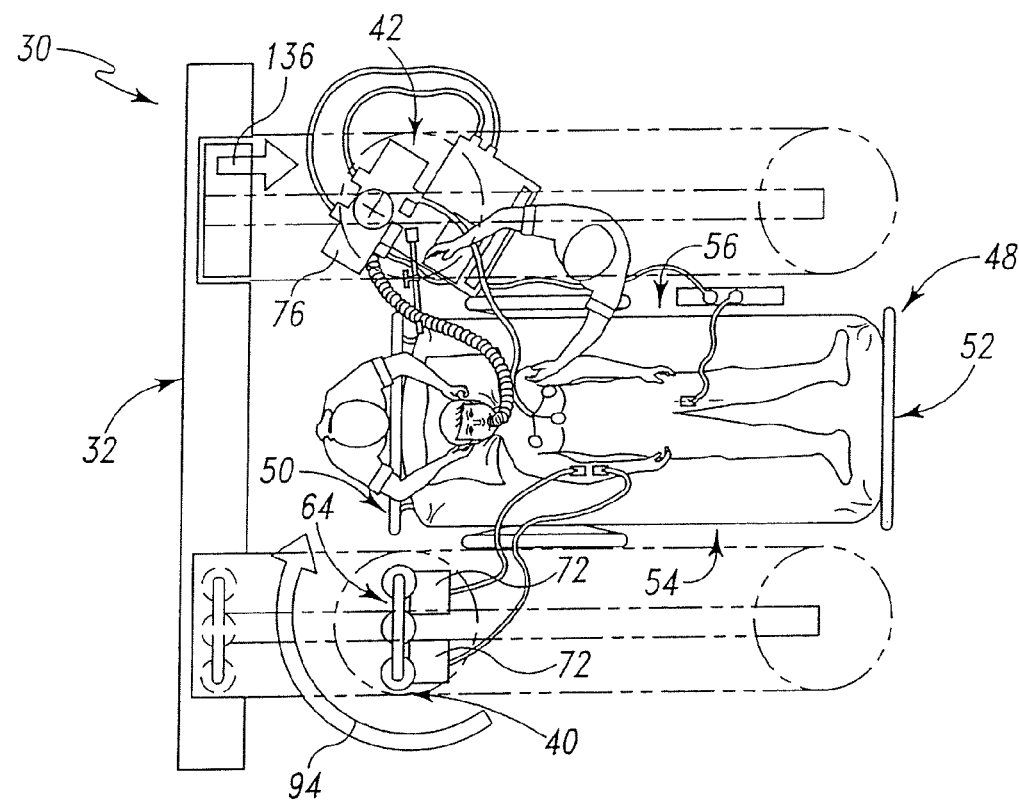
FIG. 4 is a top view, similar to FIG. 3, showing the first and second columns moved out of the first and second cavities, respectively, of the headwall unit and showing the hospital bed moved away from the headwall unit by a sufficient amount to permit a caregiver to stand between the head end of the hospital bed and the headwall unit.

A first embodiment of an architectural system 30 according to this disclosure comprises a headwall unit 32 having a first cavity 34 and a second cavity 36, a ceiling unit 38, a first column 40, and a second column 42 as shown in FIGS. 1 and 2. Columns 40, 42 hang downwardly from ceiling unit 36 and are each independently movable between respective storage positions situated within a respective cavity 34, 36 and a plurality of use positions situated outside of cavities 34, 36. Headwall unit 32 is configured for attachment to a wall 44 of a hospital room and ceiling unit 38 is configured for attachment to a ceiling 46 of the hospital room.

A hospital bed 48 is situated in the hospital room such that a head end 50 of the bed 48 is near headwall unit 32 and a foot end of the bed is spaced from head wall unit 32 as shown in FIGS. 1-4. Columns 40, 42 are spaced apart by a sufficient distance to permit hospital bed 48 to occupy the space defined between columns 40, 42 when columns 40, 42 are situated outside of cavities 34, 36 as shown, for example, in FIGS. 2 and 4. Thus, column 40 is positioned alongside a first side 54 of hospital bed 48 when outside of cavity 34 and column 42 is positioned alongside a second side 56 of hospital bed 48 when outside of cavity 36.

Figure 3:
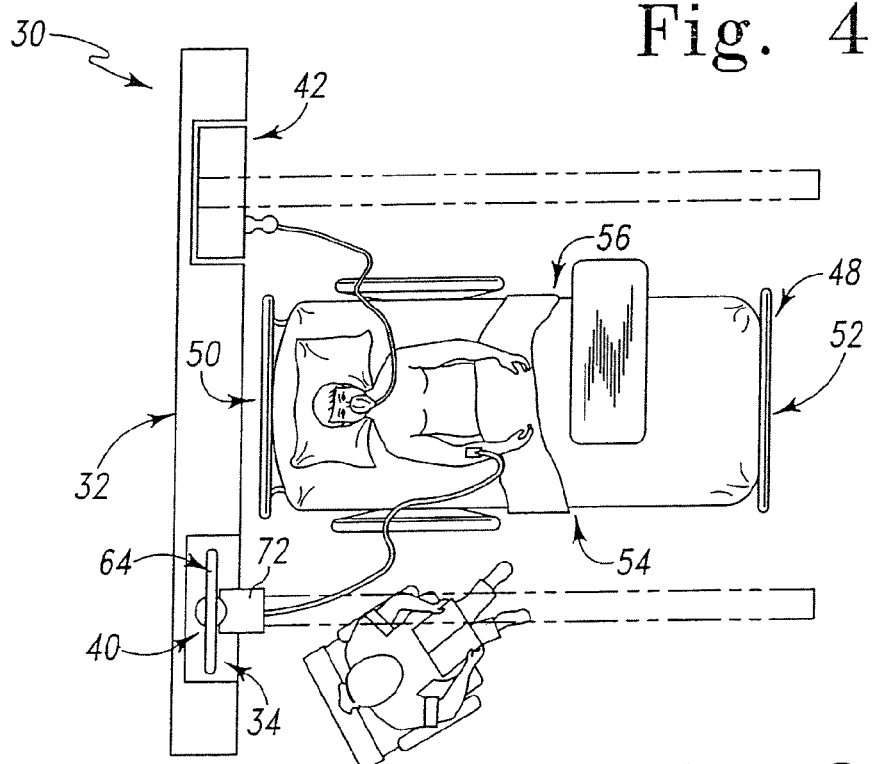
FIG. 3 is a top plan view of a portion of the architectural system of FIG. 1 showing the first and second columns received in the first and second cavities, respectively, of the headwall unit and showing a head end of the hospital bed situated in close proximity to the headwall unit.

Columns 40, 42 each carry patient-care equipment, some of which is configured to provide medical services to high acuity patients, such as critical patients requiring intensive care. Patient-care equipment needed for medium acuity patients, such as patients requiring medical gas to aid respiration and intravenous (IV) fluids are also carried on one or both of columns 40, 42. For medium acuity patients, columns 40, 42 are usually placed in cavities 34, 36 in the respective storage positions and the needed medical services are provided to the patient from columns 40, 42 as shown in FIGS. 1 and 3. Optionally, columns 40, 42 may be moved out of cavities 34, 36 for medium acuity patients. For high acuity patients, columns 40, 42 are usually moved out of cavities 34, 36 to positions alongside bed 48 so that multiple medical services are accessible to the patient and to other pieces of medical equipment as shown, for example, in FIGS. 2 and 4. For low acuity patients that do not require medical services from columns 40, 42, columns 40, 42 are usually placed in the storage positions so as to be out of the way.

Headwall unit 32 has a plurality of doors 58 that are movable between closed positions covering associated portions of columns 40, 42 and opened positions allowing access to the associated portions of columns 40, 42. For low acuity patients, doors 58 are typically closed to conceal columns 40, 42 from view. In the illustrative embodiment, each of doors 58 slides horizontally behind an associated central panel 60 of headwall unit 32. In some alternative embodiments, doors 58 slide horizontally in front of the associated central panels 60. In other alternative embodiments, doors 58 either raise or lower or pivot when moving between opened and closed positions. In the illustrative embodiment in which doors 58 slide horizontally behind panels 60, each of panels 60 is large enough to accommodate both of the associated doors 58 therebehind. It is within the scope of this disclosure for headwall unit 32 to have tracks or other surfaces (not shown) on which doors 58 slide. It is also within the scope of this disclosure for rollers (not shown) to be coupled to doors 58 and for the rollers to roll on tracks or surfaces as doors 58 move between the opened and closed positions.

In the illustrative embodiment, three doors 58 are associated with cavity 34 to cover top, middle, and lower portions of cavity 34 and three doors 58 are associated with cavity 36 to cover top, middle, and lower portions of cavity 36. In alternative embodiments, more or less than three doors are provided for covering respective cavities 34, 36. Optionally, locking mechanisms (not shown) are mounted to each door 58 for locking the respective door in the closed position to prevent a patient or any other unauthorized person from opening doors 58 to gain access to the equipment mounted on columns 40, 42.

Figure 8:
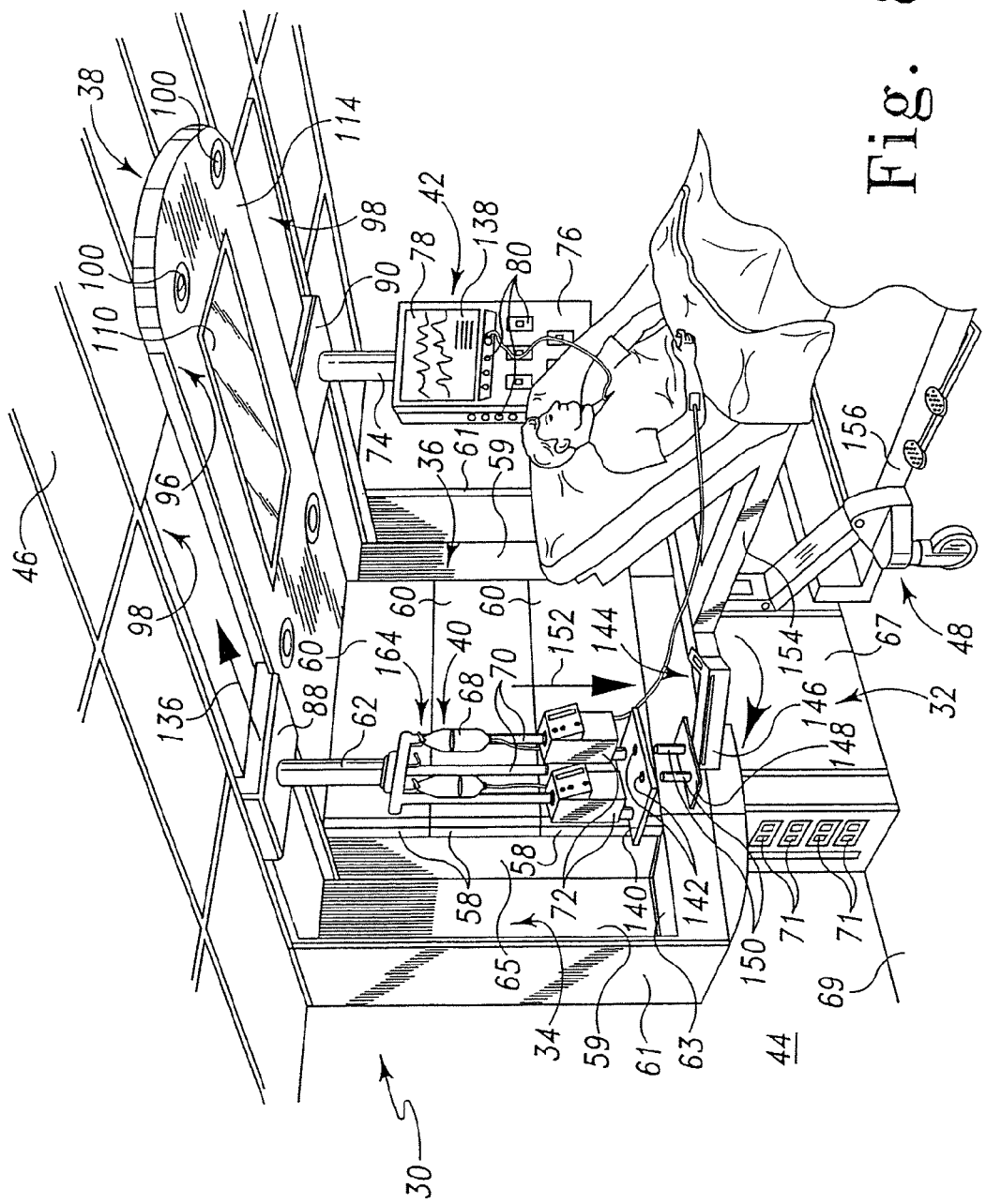
FIG. 8 is a perspective view of the architectural system of FIG. 1 showing the first column carrying an IV rack having a bottom plate arranged for coupling to a pair of upright posts that are mounted to a distal end of a support arm extending from a bed frame of the hospital bed.

Headwall unit 32 has a frame (not shown) to which central panels 60 couple. Headwall unit 32 has other panels or walls, such as a vertical back wall 59 and a pair of outer side walls 61 that extend from back wall in perpendicular relation therewith. In addition, headwall unit 32 has horizontal walls 63 that underlie cavities 34, 36 and inner side walls 65 that are spaced from, but parallel with, walls 61 as shown in FIG. 8. Cavities 34, 36 are defined, in part, by walls 59, 61, 63, 65. One or more of walls 59, 61, 63, 65 are coupled to the frame of headwall unit 32. In the illustrative embodiment, headwall unit 32 includes a lower portion 67 that is situated between a floor 69 of the hospital room and the portion of headwall unit 32 having central panels 60 associated therewith as shown in FIG. 8. A set of auxiliary medical service outlets 71 are coupled to lower portion 67. In addition, the portions of headwall unit 32 in which cavities 34, 36 are defined overhang underlying portions of floor 69 that are laterally outward of lower portion 67.

Figure 9:
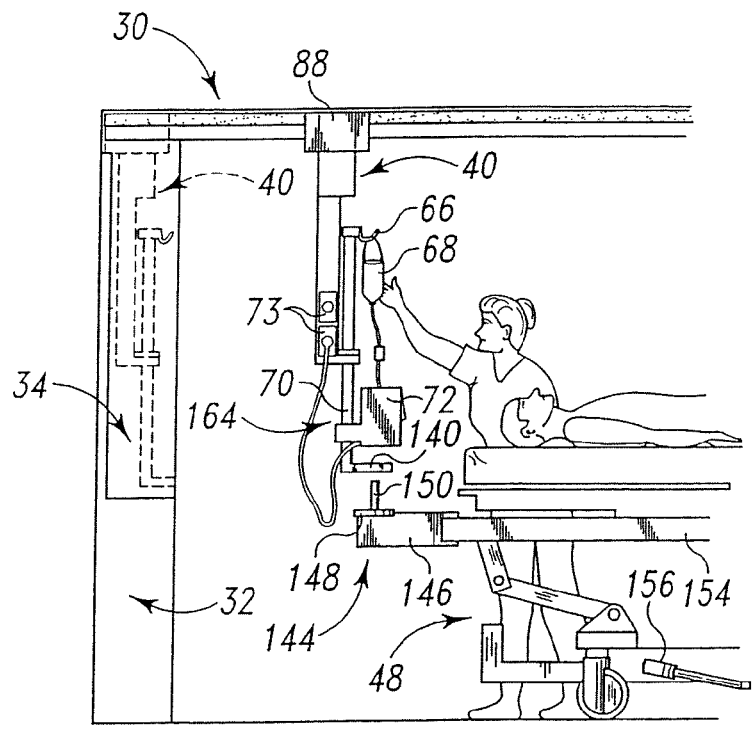
FIG. 9 is a side elevation view of the architectural system of FIG. 8 showing the first column (in solid) supporting the IV rack above the upright posts and showing the first column (in phantom) supporting the IV rack in the first cavity of the headwall unit.
Figure 10:
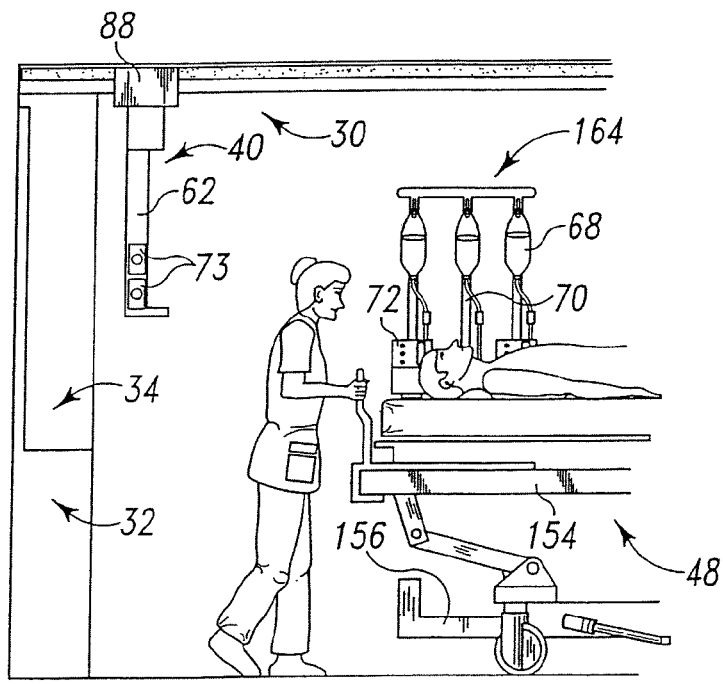
FIG. 10 is a side elevation view, similar to FIG. 9, showing the IV rack decoupled from the first column and coupled to the hospital bed to be transported with the hospital bed.

As previously mentioned, columns 40, 42 carry patient-care equipment. Column 40 is configured to have patient-care equipment attached thereto and detached therefrom, whereas column 42 has patient-care equipment integrated therewith as shown in FIGS. 1 and 2. In the illustrative example, column 40 has a vertical arm 62 and an IV rack 64 coupled to vertical arm 62 by suitable couplers such as, for example, clamps, brackets, latches, grippers, or hooks. IV rack 64 has one or more hooks 66 to which IV bags 68 couple and one or more poles 70 to which infusion pumps 72 couple. It is within the scope of this disclosure for any type of medical equipment capable of coupling to an IV pole to be coupled to IV rack. As shown in FIGS. 9 and 10, one or more medical service outlets 73 are mounted to arm 62 of column 40. Services accessible via outlets 73 include electrical services, such as electrical power and data transfer, and pneumatic services, such as medical gases or suction. Illustratively, electrical power is provided to infusion pump 72 from one of outlets 73 as shown in FIG. 9.

Figure 5:
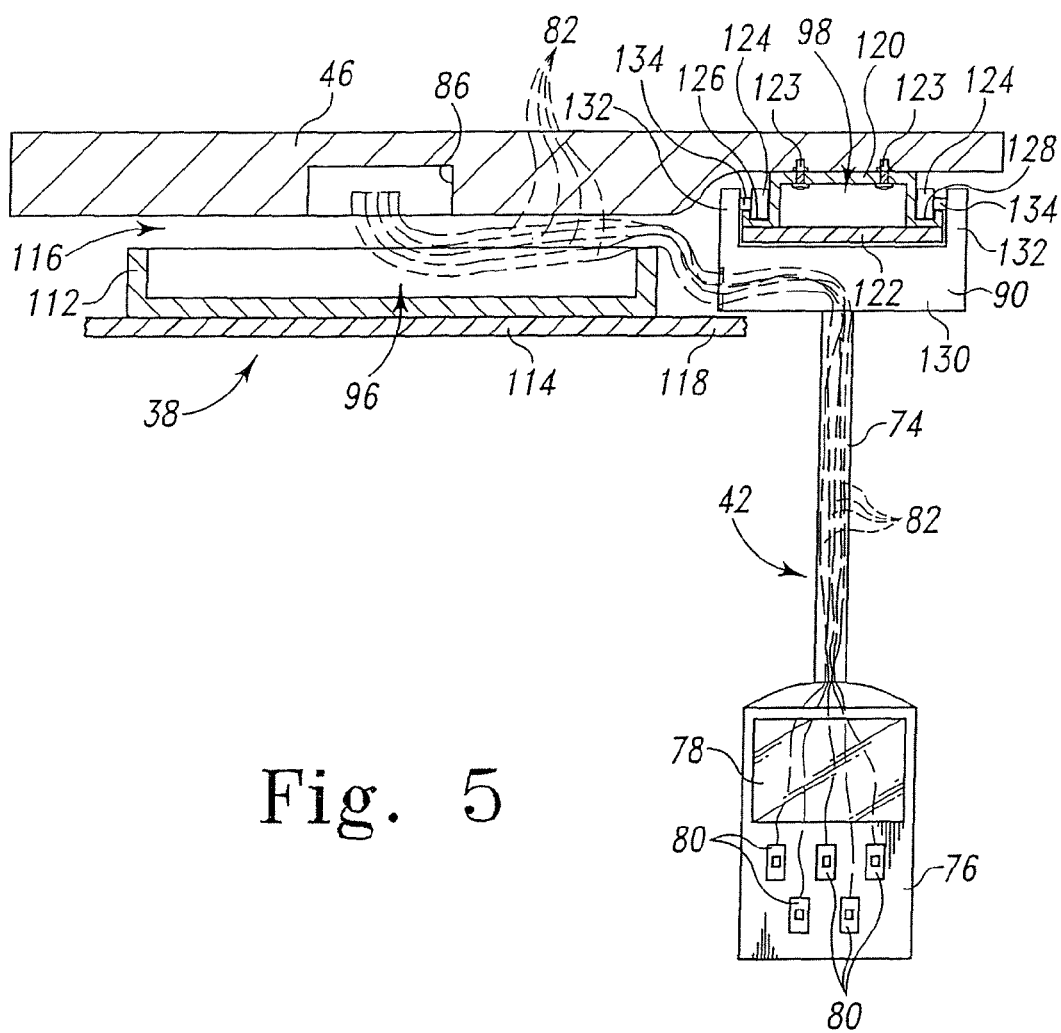
FIG. 5 is a transverse sectional view of a portion of the architectural system of FIG. 1 showing rollers of the second column engaging a track of the ceiling unit and showing medical service lines (in phantom) extending from each of the medical service outlets, through the second column, and through the ceiling unit.
Figure 6:
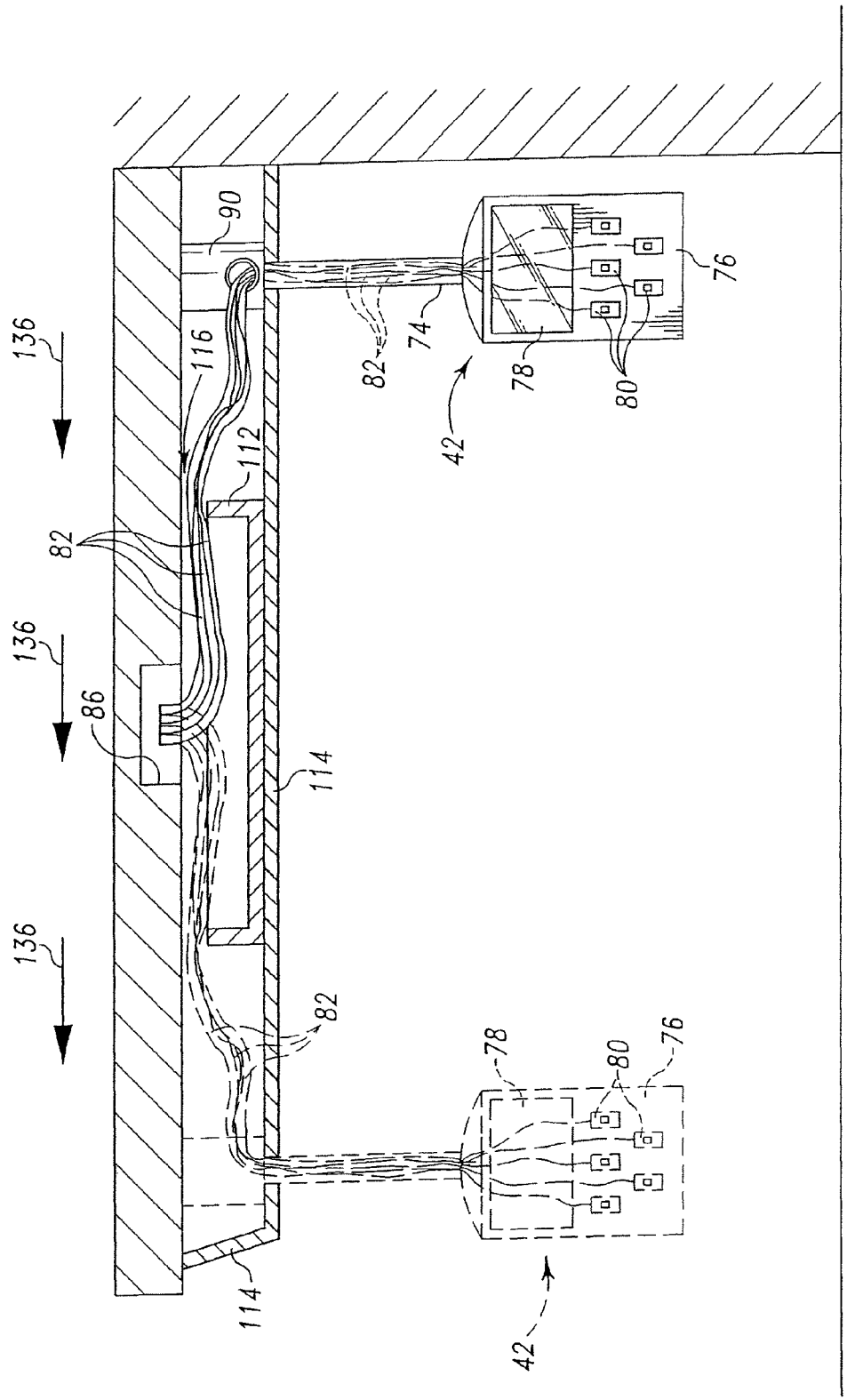
FIG. 6 is a longitudinal sectional view of a portion of the architectural system of FIG. 1 showing the second column being movable between a first position (in solid) in close proximity to the headwall unit and a second position (in phantom) spaced from the headwall unit and showing the medical lines being routed into a central region of the ceiling unit to accommodate the movement of the second column between the first and second positions.
Figure 7:
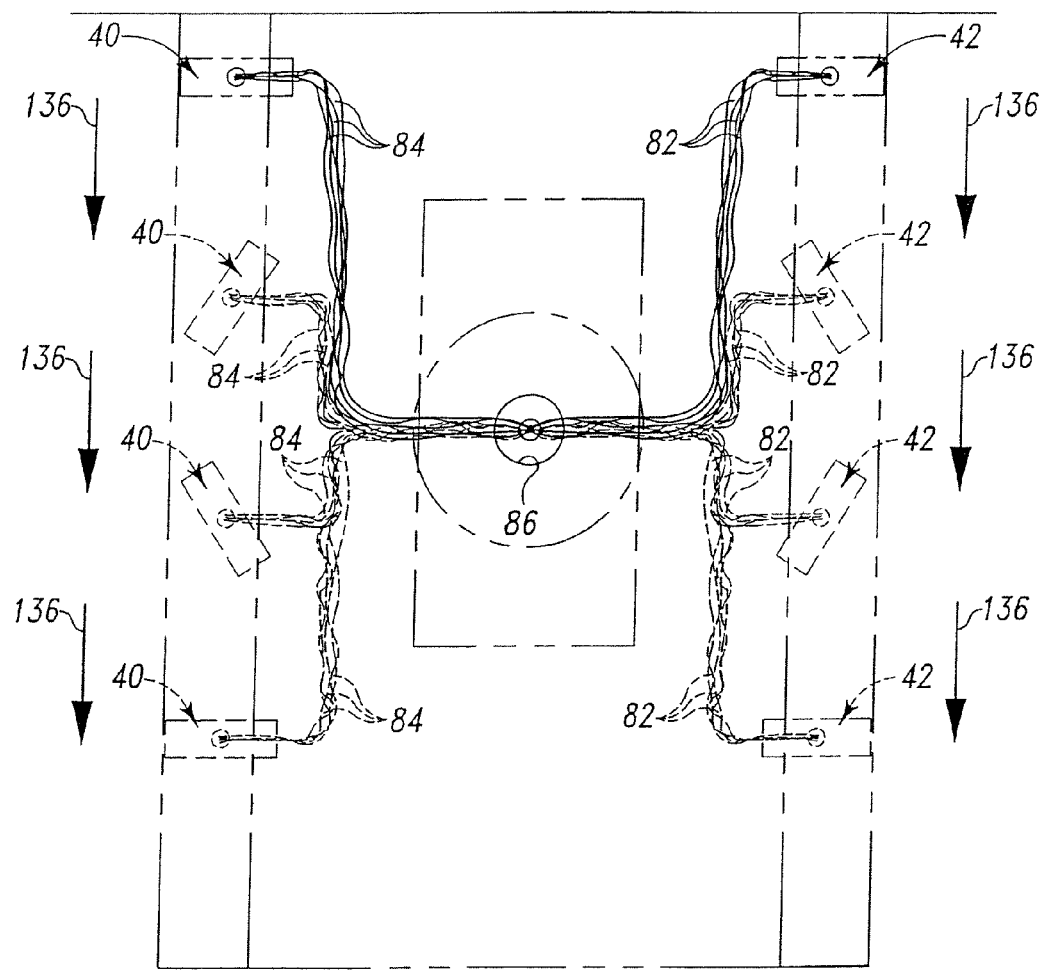
FIG. 7 is a top plan view of a portion of the architectural system of FIG. 1 showing the first and second columns in a number of positions and showing the routing of the medical lines from the central region of the ceiling unit to the first and second columns.

In the illustrative example, column 42 has a vertical arm 74 and a housing 76 coupled to arm 74. A display screen 78 is coupled to an upper portion of housing 76 and a plurality of medical service outlets 80 are coupled to a lower portion of housing 76. Services available via outlets 80 include similar electrical and/or pneumatic services as are available from outlets 73. Service-delivery lines 82 are routed from each of outlets 80 through housing 76 and arm 74 of column 42 and through ceiling unit 38 as shown in FIGS. 5-7. In addition, service-delivery lines 84 are routed from each of outlets 73 through arm 62 of column 40 and through ceiling unit 38 as shown in FIG. 7. In addition, lines 82, 84 are routed into ceiling 46 through an opening 86 that is formed in ceiling above a central region of ceiling unit 38.

Column 40 has a carriage 88 to which arm 62 is coupled and column 42 has a carriage 90 to which arm 74 is coupled as shown in FIG. 2. In some embodiments, arm 62 and IV rack 64 (or any other patient-care equipment coupled to arm 62) are pivotable about a vertical axis relative to carriage 88 in a first direction as indicated by arrow 92, shown in FIG. 2, and in an opposite, second direction as indicated by arrow 94, shown in FIG. 4. In other embodiments, arm 62 is fixed relative to carriage 88 but the coupler to which IV rack 64 (or other patient-care equipment) couples is pivotable relative to arm 64 in directions 92, 94. Similarly, in some embodiments, arm 74 and housing 76 are pivotable about a vertical axis relative to carriage 90 in first and second directions and, in other embodiments, arm 74 is fixed relative to carriage 90 and housing 76 is pivotable relative to arm 74 about a vertical axis in first and second directions. Various angular orientations of columns 40, 42 about their respective vertical axes are shown in FIG. 7. In illustrative embodiments, the vertical axes about which IV rack 64 and housing 76 pivot extend through associated vertical arms 62, 74.

Ceiling unit 38 of system 30 has a central portion or canopy 96 and a pair of side portions or tracks 98 as shown, for example, in FIGS. 1 and 2. Canopy 96 generally overlies bed 48, whereas tracks 98 are situated laterally outward of canopy 96. Canopy 96 has a set of lights 100 integrated therein. Lights 100 include reading lights and/or examination lights. In some embodiments, reading lights comprise standard incandescent or fluorescent bulbs, whereas examination lights comprise, for example, halogen bulbs and color-correction filters. All types of reading lights and examination lights are contemplated by this disclosure as being included in ceiling unit 38. Illustrative canopy 96 also has a display screen 110 integrated therein. In other embodiments, display screen 110 is omitted. Various images, such as family photos and nature scenes may be displayed on screen 110.

Ceiling unit 38 has a first or proximal end coupled to or overlying portions of headwall unit 32 and an opposite, distal end that is spaced apart from headwall unit 32. Thus, ceiling unit 38 extends from headwall unit 32 along ceiling 46 of the hospital room. Canopy 96 comprises a housing or frame 112 and a cosmetic cover or panel 114 that couples to frame 112 as shown in FIGS. 5 and 6. Frame 112 includes portions (not shown) that couple to ceiling 46 and/or to headwall unit 32 with suitable couplers such as, for example, bolts, rivets, welds, clamps, tabs, and the like. The various pieces of equipment carried by ceiling unit 38, including lights 100 and screen 110, are mounted to frame 112 and extend through appropriately sized openings formed in panel 114. In addition, portions of lines 82, 84 loosely drape over frame 112 and cover 114 as shown in FIGS. 5 and 6. Lines 82, 84 are routed through suitably sized slots or spaces 116 that are provided between frame 112 and ceiling 46, or alternatively, between other portions of ceiling unit 38 through which lines 82, 84 are routed.

As columns 40, 42 move between the storage and various use positions, lines 82, 84 move relative to ceiling unit 38 in a somewhat random manner. However, frame 112 and cover 114 are situated beneath portions of lines 82, 84 to shield these portions of lines 82, 84 from view. Other portions of lines 82, 84 are shielded from view by columns 40, 42, respectively. In the illustrative embodiment, panel 114 has lateral side portions 118 that underlie portions of carriages 88, 90 as shown in FIG. 5 with respect to carriage 90. Side portions 118 further shield lines 82, 84 from view. Lines 82, 84 have sufficient slack in the interior region of canopy 96 to permit columns 40, 42 to move from the respective storage positions to the respective farthest use positions adjacent the distal end of associated tracks 98. It is within the scope of this disclosure for one or more line management mechanisms, such as strain reliefs, hoses, conduits, cables, cable ties, articulating segmented channels, and the like, to be coupled to lines 82, 84 either to guide or control the movement of lines 82, 84 or to restrain the movement of lines 82, 84 in a desired manner as columns 40, 42 move between the storage positions in cavities 34, 36, respectively, and the various positions outside of cavities 34, 36.

Each illustrative track 98 comprises a track member 120 and a cosmetic cover or panel 122 coupled to the respective member 120 as shown in FIG. 5. Suitable couplers, such as illustrative bolts 123, couple track member 120 to ceiling 46 or, in alternative embodiments, to portions of frame 112 that overlie tracks 98. The proximal ends of track members 120 overlie respective cavities 34, 36 to permit carriages 88, 90 to move along track members 120 into cavities 34, 36, respectively. Columns 40, 42 each comprise a plurality of rollers 124 some of which engage a first roller-engaging surface 126 of the associated member 120 and others of which engage a second roller-engaging surface 128 of the associated member 120 as also shown in FIG. 5. Surfaces 126, 128 are each elongated and extend generally perpendicularly relative to wall 44 of the hospital room. Thus, surfaces 126 are parallel with surfaces 128. In addition, surfaces 126, 128 lie in a common horizontal plane. In some alternative embodiments, track members 120 are curved and in other alternative embodiments, track members 120 are not parallel to each other.

Carriages 88, 90 are each somewhat U-shaped having central portions 130 that underlie track members 120 and having a pair of side portions 132 that extend upwardly from respective central portions 130 such that track members 120 are situated between respective side portions 132. Rollers 124 each have shafts 134 that are coupled to side portions 132 and that extend horizontally therefrom in a cantilevered manner toward associated track members 120. As columns 40, 42 move along tracks 98, such as, for example, in directions 136 away from respective cavities 34, 36 as shown in FIGS. 2, 4, and 6-8, rollers 124 roll along corresponding surfaces 126, 128. Of course, rollers 124 also roll along surfaces 126, 128 when columns 40, 42 move along tracks 98 in directions opposite to directions 136.

According to this disclosure, housing 76 carries electrical circuitry to control the operation of display screen 78. In some embodiments, housing also carries electrical circuitry to control the operation of display screen 110 and lights 100. In other embodiments, some or all of the circuitry that controls the operation of screens 78, 110 and lights 100 are housed in portions of head wall unit 32. Such circuitry includes for example, one or more of a microprocessor or microcontroller, input/output circuitry, signal conditioning circuitry, signal conversion (analog-to-digital and/or digital-to-analog) circuitry, power conditioning circuitry, memory circuitry, and the like. In addition, a user interface is provided on column 42 to permit a user to enter commands and retrieve data for display on screen 78. In the illustrative embodiment, screen 78 is a touch screen and the user input on column 42 comprises user input buttons 138 displayed on screen 78 as shown, for example, in FIG. 8.

In some embodiments, the electrical circuitry that controls the operation of display screen 78 is coupled to the hospital's computer network or ethernet. In such embodiments, any of the information available on the network is viewable on display screen 78. For example, a caregiver is able to retrieve a patient's medical records (e.g. laboratory test results, medical diagnosis, patient charts, x-rays, and so on) from the network for viewing on screen 78. In addition, patient point-of-care data, such as vital signs data (e.g. heart rate, blood pressure, neurological activity, respiration rate, patient temperature, pulse oximetry) and data associated with the operation of patient-care equipment (e.g. data from one or more ventilators, infusion pumps, electrocardiographs, electroencephalographs), may be displayed on screen 78. Thus, the circuitry associated with screen 78 is programmed and/or configured to receive and process various types of data signals indicative of the information to be displayed on screen 78. It is within the scope of this disclosure for all types of data associated with the care of a patient to be displayed on screen 78. In addition, it is within the scope of this disclosure for screen 78 to display multiple types of data simultaneously, such as in a split screen format. Furthermore, in those embodiments in which the hospital computer network is coupled to the Internet, then information accessible via the Internet is also able to be displayed on screen 78.

An alternative IV rack 164 that is attachable to and detachable from vertical arm 62 is shown in FIGS. 8-10. IV rack 164 is similar to IV rack 64 and therefore, where appropriate, like reference numerals are used to denote components of IV rack 164 that are substantially similar to like components of IV rack 64. As was the case with IV rack 64, IV rack 164 couples to arm 62 with suitable couplers such as, for example, clamps, brackets, latches, grippers, hooks, or the like. The main difference between IV rack 164 and IV rack 64 is that IV rack 164 has a horizontal plate 140 coupled to the lower ends of poles 70. Plate 140 has one or more openings or sockets 142 as shown in FIG. 8.

An arm assembly 144 for carrying IV rack 164 includes an arm 146 coupled to bed 48 for pivoting movement about a vertical axis, a horizontal plate 148 coupled to arm 144, and a pair of posts 150 extending vertically upwardly from plate 146. Arm 146 is movable to a first position extending laterally outwardly from bed 48 to support plate 148 and posts 150 at a location which permits coupling of IV rack 164 to arm assembly 144 as shown in FIGS. 8 and 9. Vertical arm 62 and carriage 88 are movable along track 98 to position IV rack over plate 148 and posts 150. In addition, IV rack 164, or the combination of arm 62 and IV rack 164, is rotatable about the vertical axis extending through arm 62 to orient IV rack 164 such that sockets 142 are aligned with posts 150. After IV rack 164 is properly oriented over arm assembly 144, as shown in FIGS. 8 and 9, IV rack 164 is lowered in the direction of arrow 152, shown in FIG. 8, so that posts 150 are received in sockets 142 and so that plate 140 rests upon plate 148, thereby to couple IV rack 164 to arm assembly 144.

In some embodiments, the coupler that couples IV rack 164 to arm 62 is movable vertically relative to arm 62 to permit raising and lowering of IV rack 164 and, in other embodiments, arm 62 comprises telescoping segments that permit raising and lowering of IV rack 164. Alternatively, IV rack 164 is decoupled from arm 62 and is lowered manually onto arm assembly 144. It is also within the scope of this disclosure for an upper frame 154 of bed 48 to be lifted relative to a base 156 of bed 48 so that posts 150 enter into openings 142 and so that plate 148 moves into engagement with plate 140. In some embodiments, additional mechanisms (not shown), such as latches on plate 142 or plate 150, pins that extend through posts 150, caps that snap or thread onto posts, clamps that grip plates 140, 148, and the like, are provided to lock IV rack 164 to arm assembly 144. After IV rack 164 is coupled to arm assembly 144 and decoupled from arm 62, arm 146 is pivotable relative to bed 48 to a second position having IV rack 164 supported alongside bed 48 as shown in FIG. 10. Thus, bed 48 and IV rack 164 coupled to bed 48 are transportable through the hospital without needing to disconnect IV lines from the patient carried by bed 48.

Referring now to FIGS. 11-14, an alternative architectural system 230 has a headwall unit 232 and a ceiling unit 238 that are substantially similar to headwall unit 32 and ceiling unit 38, respectively, of system 30. Therefore, where applicable, like reference numerals are used to denote components of system 230 that are substantially similar to like components of system 30. One of the differences between system 230 and system 30 is that headwall unit 232 of system 230 has a pair of auxiliary cavities 234, 236 (see FIGS. 12 and 14) that are laterally outboard of cavities 34, 36, respectively. A pair of doors 235, 237 are each independently movable between a closed position, shown in FIG. 11, in which the respective cavity 234, 236 and any items or equipment stored therein are inaccessible and an opened position in which the respective cavity 234, 236 and any items or equipment stored therein are accessible. In the illustrative embodiment, doors 235, 237 pivot about respective vertical axes when moving between the opened and closed positions. Suitable locking mechanisms are provided in some embodiments for locking doors 235, 237 in the closed positions. As was the case with system 30, doors 58 of system 230 are movable to open and close cavities 34, 36.

Figure 11:
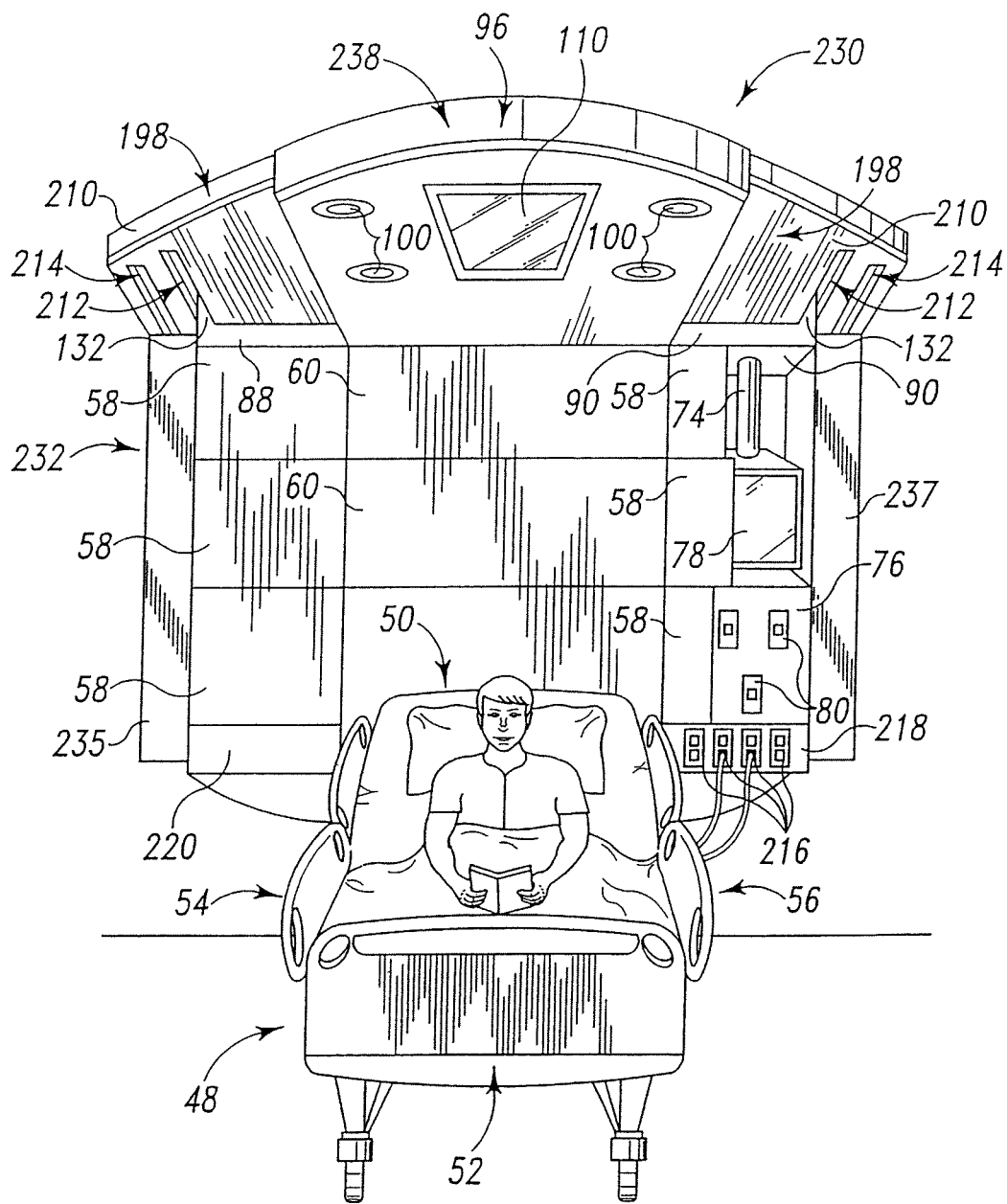
FIG. 11 is a perspective view of a first alternative embodiment of an architectural system according to this disclosure showing the ceiling unit having lateral extensions for supporting auxiliary equipment laterally outward of the first and second columns, a first set of door panels covering the first column, and a second set of door panels being opened by varying amounts to partially uncover various portions of the second column.

Headwall unit 232 has additional medical service outlets 216 mounted on a pair of lower vertical panels 218 which are situated beneath the lowermost pair of doors 58 as shown in FIGS. 11, 14, and 14. Headwall unit 232 also has a pair of lower doors 220 that are movable between respective first positions in which doors 220 cover the associated outlets 216 and respective opened positions in which outlets 216 are uncovered for use. It is within the scope of this disclosure for system 30 to also have outlets 216, panels 218, and doors 220. In some embodiments, auxiliary outlets 71 and outlets 216 are included in the headwall unit and, in other embodiments, only one or the other set of outlets 71, 216 are included in the headwall unit.

Another of the differences between system 230 and system 30 is that ceiling unit 238 of system 230 has tracks 198 which are wider than tracks 98 of system 30. Thus, tracks 198 extend laterally outward from canopy 96 of ceiling unit 238 by a greater amount than tracks 98 extend laterally outward from canopy 96 of ceiling unit 38. Each of tracks 198 have a cosmetic cover or panel 210. Each panel 210 has a first elongated slot 212 and a second elongated slot 214. In the illustrative embodiment, slots 212 are parallel with slots 214. Each slot 212 receives a respective side portion 132 of the associated carriage 88, 90 of the respective column 40, 42. Thus, provision of slots 212 in covers 210 allows columns 40, 42 of system 230 to move without interference from panels 210 between the respective storage positions within cavities 34, 36 and the various positions outside of cavities 34, 36.

In some embodiments, slots 214 are situated beneath respective track members (not shown) that are configured to support auxiliary equipment which is moved out of auxiliary cavities 234, 236 and, in other embodiments, auxiliary equipment is situated above slots 214. In the example shown in FIG. 12, a privacy curtain 240 is movable from a storage position in which curtain 240 is situated within cavity 236 to a use position in which a majority of curtain 240 is drawn out of cavity 236. In the use position, curtain 240 hangs downwardly from substantially the entire length of the track member situated above the respective slot 214. Illustrative curtain 240 has a flexible curtain panel 242, a plurality of sliders 244, and a plurality of strands 246. Each strand 246 extends between panel 242 and a respective slider 244. Sliders 244 are movable along the track member situated above slot 214. Thus, when curtain 240 is in the storage position, all of sliders 244 are grouped together within cavity 236 and when curtain 240 is in the use position, sliders 244 are spaced apart along the length of slot 214.

In the example shown in FIG. 13, a privacy curtain 250 is extendable downwardly out of the associated slot 214 to a use position and is retractable upwardly through slot 214 to a storage position. Curtain 250 has a flexible curtain panel 252 and a bottom member 254 coupled to a bottom portion of panel 252. Member 254 adds weight to curtain 250 to prevent excessive movement of curtain 250 away from a vertical hanging configuration as shown in FIG. 13. A rotatable shaft (not shown) on which panel 252 winds when retracting and unwinds when extending is situated above slot 214. In some embodiments, a motor (not shown) is coupled to shaft and is operated to rotate the shaft in the appropriate directions to wind and unwind panel 252. In such embodiments, a user input, such as one or more switches, buttons, levers, or the like, is accessible on headwall unit 232 to control the motor. In alternative embodiments, curtain 250 is extended and retracted manually, similar to the manner in which conventional window shades are pulled down to cover a window and are manipulated so that a spring causes an associated shaft to wind up the window shade.

In the example shown in FIG. 14, an auxiliary IV pole 160 hangs downwardly from a carriage 162 that is slideable along a track member (not shown) which is situated above the respective slot 214. Pole 160 and carriage 162 are movable between a storage position in cavity 234 and a number of use positions outside of cavity 234. One or more hooks 166 are coupled to pole 160 for holding IV bags 68. In the illustrative embodiment, a dedicated infusion pump 172 is mounted to a bottom end of pole 160. In alternative embodiments, infusion pumps 72 are attachable to and detachable from other portions of pole 160. It is within the scope of this disclosure for any type of patient-care equipment that is capable of coupling to an IV pole to be coupled to pole 160.

Although curtain 240 is shown in FIG. 12 has being associated with cavity 236 and although pole 160 is shown in FIG. 14 as being associated with cavity 234, it is within the scope of this disclosure for curtains, IV poles, and any other type of track-mounted auxiliary equipment, such as exam lights, water hoses, suction hoses, traction devices, and the like, to be associated with either of cavities 234, 236. In addition, it is within the scope of this disclosure for the various walls of headwall unit 232 that bound cavities 234, 236, such as back wall 259, side wall 261, and bottom wall 263 (see FIG. 14), to be appropriately sized and configured so that cavities 234, 236 are large enough to receive the track mounted equipment to be stored therein. In addition, in those embodiments having auxiliary equipment, such as curtain 250 that extends and retracts out of slots 214, then cavities 234, 236 may have storage shelves therein.

Figure 15:
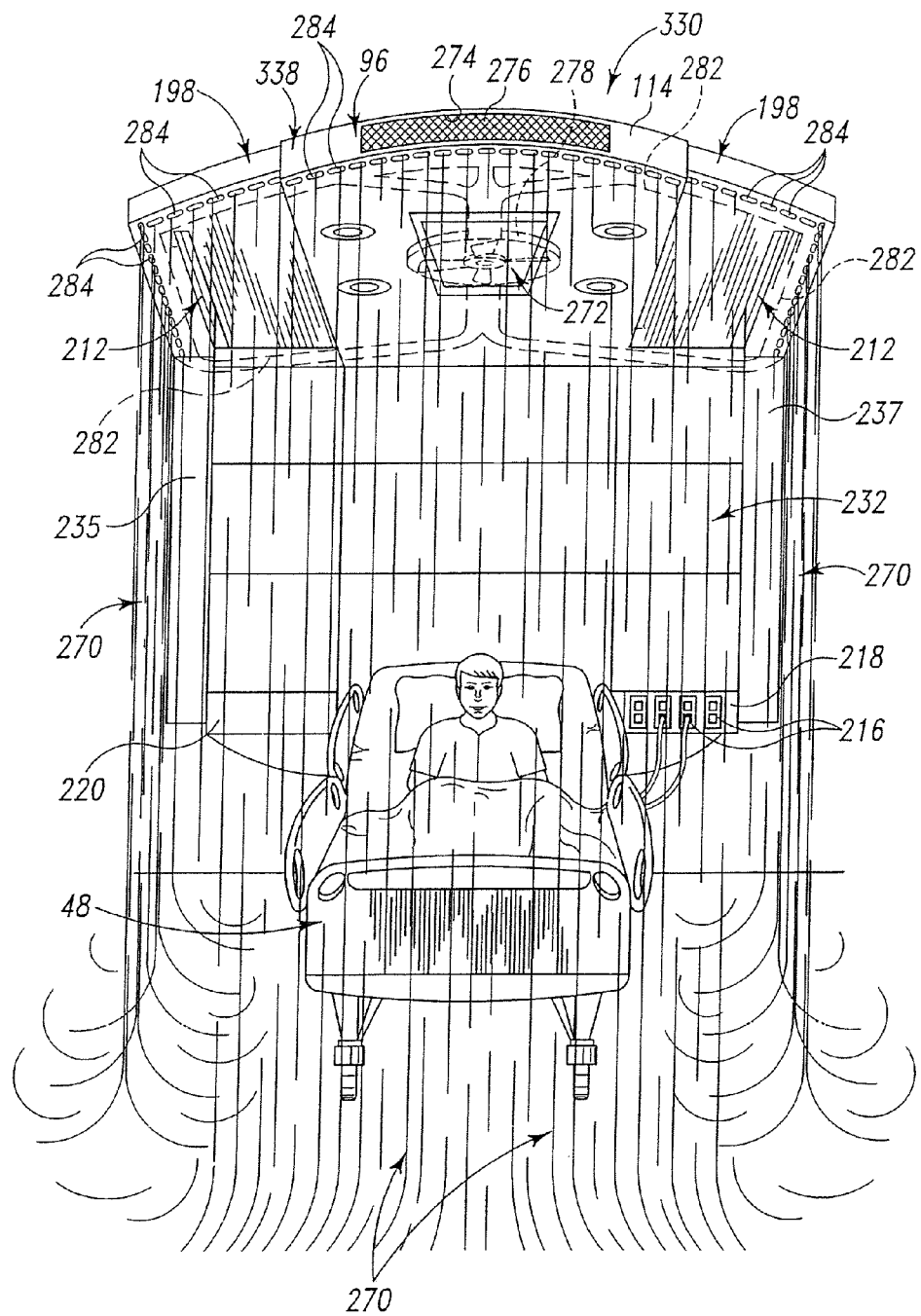
FIG. 15 is a perspective view of a second alternative embodiment of an architectural system according to this disclosure showing a plurality of openings formed in a perimetral region of the ceiling unit and showing air curtain generation equipment (in phantom) operating to move air out of the plurality of openings to form vertical air curtains along the foot end and opposite sides of the hospital bed.
Figure 16:
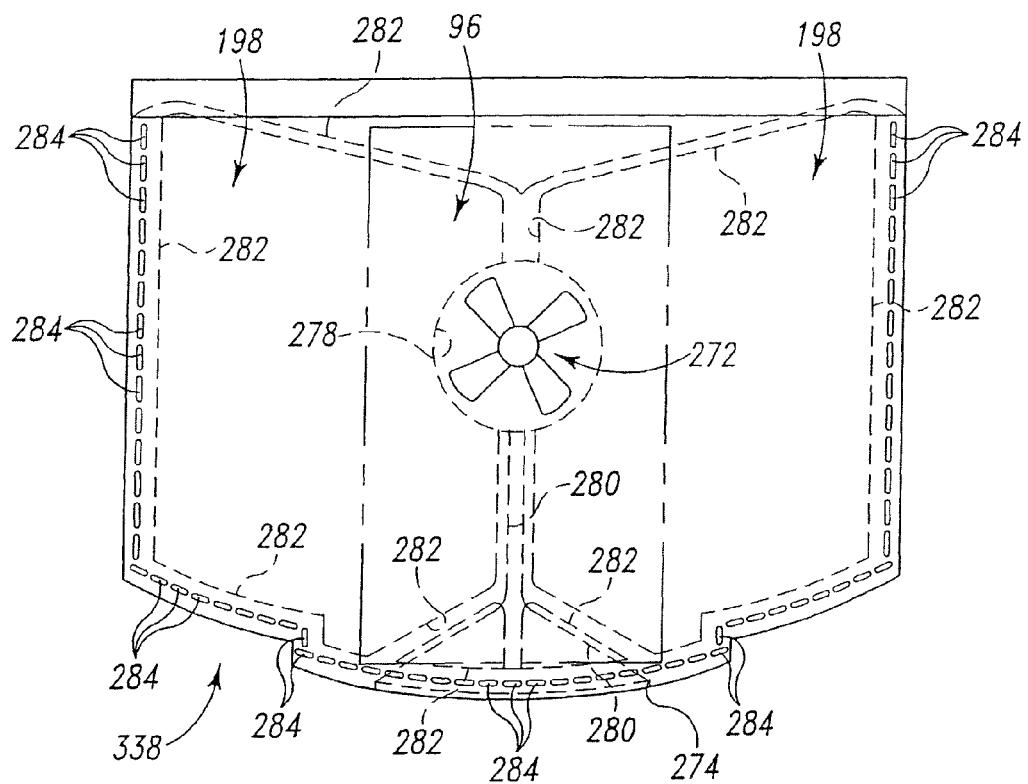
FIG. 16 is a bottom plan view of the ceiling unit of FIG. 15 showing, in phantom, a fan and a set of channels through which air moves to reach the plurality of openings.

Referring now to FIGS. 15 and 16, an alternative architectural system 330 includes a headwall unit 232, that is substantially similar to headwall unit 232 of system 230, and a ceiling unit 338 from which a set of air curtains 270 are directed downwardly around three sides of hospital bed 48. In the illustrative embodiment, the set of air curtains are adjacent foot end 52 and sides 54, 56 of bed 48. A suitable amount of space is provided between air curtains 270 and bed 48 to permit a caregiver to stand therebetween. Air curtains 270 provide a modicum of environmental isolation for the patient on bed 48. Thus, air borne contaminants outside the patient space bounded by air curtains 270 are prevented from entering the patient space. In some embodiments, air curtains 270 are heated and/or humidified to control the temperature and humidity of the patient space. In such embodiments, heating equipment (not shown) and/or humidifying equipment (not shown) is housed in either ceiling unit 338 or headwall unit 232 or both.

An air curtain generator 272, such as a fan, blower, pump, or the like, is housed in canopy 96 of ceiling unit 338 as shown in FIGS. 15 and 16. An air-intake opening 274 is formed in cover 114 of canopy 96 and an air filter 276 covers opening 274 to filter contaminants from the ambient environment. Air curtain generator 272 is situated in a central chamber 278 of canopy 96 and an air-inlet duct 280 extends from opening 274 to chamber 278. A network of air-outlet ducts 282 extend from chamber 278 throughout ceiling unit 338, including along the outer regions of lateral side portions 198 and including along the front distal regions of canopy 96 and portions 198. Duct 280 overlies some of ducts 282 as shown in FIG. 16. In the illustrative embodiment of system 330, a plurality of air-exit openings or slots 284 are formed along the side and front peripheral regions of the underside of ceiling unit 338. Operation of air curtain generator 272 moves air from the ambient environment through each of filter 276, duct 280, chamber 278, ducts 282, and openings 284 to form air curtains 270.

A controller (not shown) housed in ceiling unit 338 or headwall unit 232 or both operates to control air curtain generator 272, the heating equipment (if any), and the humidification equipment (if any). A user interface is provided on one or both of columns 40, 42 or on headwall unit 232. A user inputs operational parameters, such as, for example, fan speed (high, medium, low), air temperature, and air humidity, to the controller via the user interface. In addition, system 330 has various sensors, such as, for example, a fan speed sensor, a temperature sensor, and a humidity sensor that provides feedback to the controller so that appropriate commands from the controller can be provided to air curtain generator 272, the heating system, and the humidification system to adjust the operation of these devices, if appropriate.

Figure 17:
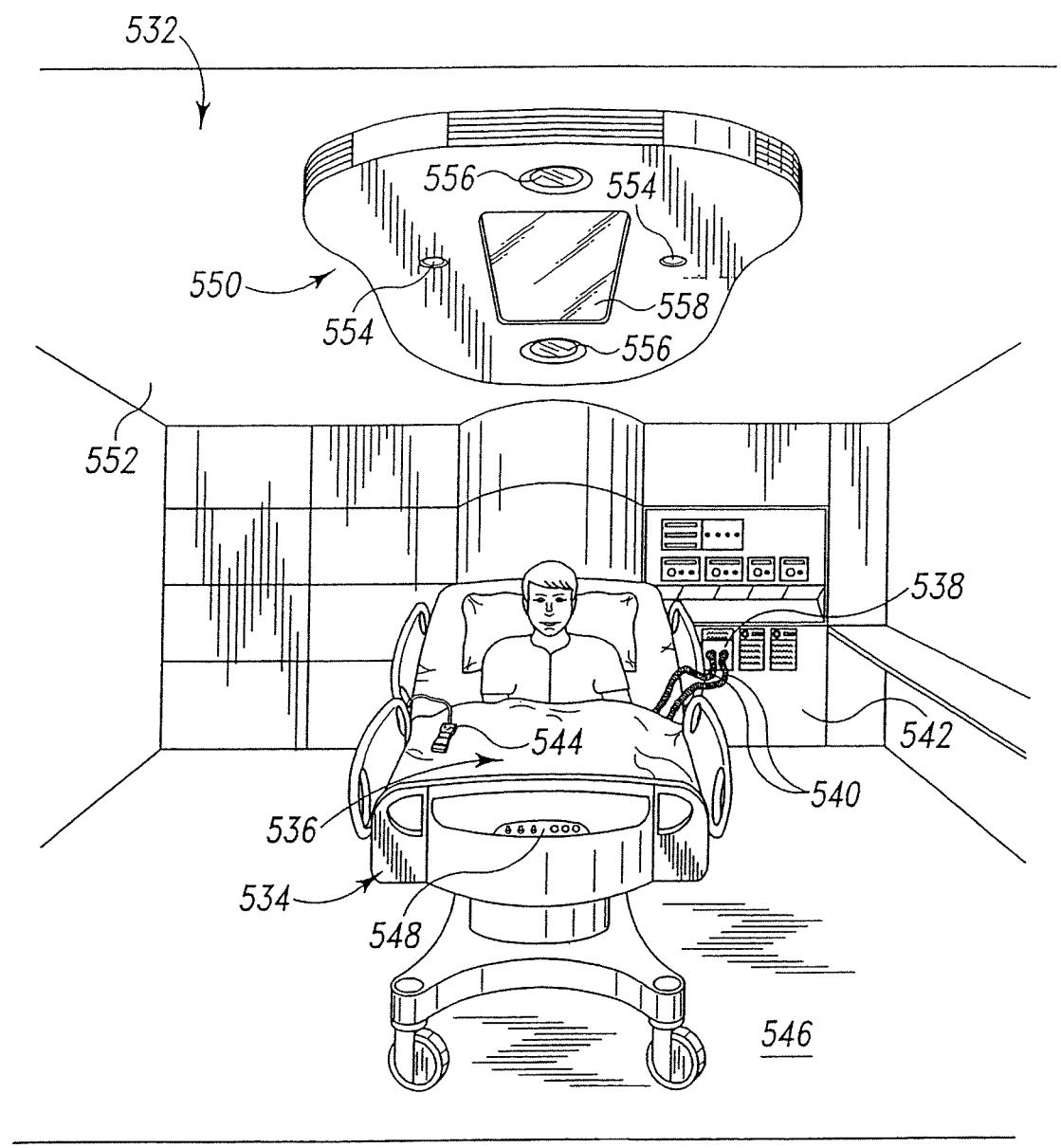
FIG. 17 is a perspective view of an environmentally-controlled hospital room showing a patient supported by a hospital bed in the room, a disposable thermoregulation blanket covering a portion of the patient, the disposable thermoregulation blanket being coupled via a hose to a thermoregulation unit housed in a headwall of the hospital room, and an environmental control canopy coupled to a ceiling of the hospital room above the hospital bed.

According to one aspect of the present disclosure, a patient rests on a hospital bed 534 in an environmentally-controlled hospital room 532 as shown in FIG. 17. Covering the patient is a disposable heating/cooling blanket 536. Blanket 536 is coupled via a pair of heating/cooling hoses 540 to a heating/cooling unit 538 housed in a headwall 542 of room 532. When the patient is to be cooled, unit 538 operates to provide a cooling medium, such as cool air or cool liquid, through one of hoses 540 to blanket 536 and the other of hoses 540 provides the cooling medium back to unit 538 after circulation of the cooling medium through blanket 536. When the patient is to be heated, unit 538 operates to provide a heating medium, such as heated air or heated liquid, through one of hoses 540 to blanket 536 and the other of hoses 540 provides the cooling medium back to unit 538 after circulation of the heating medium through blanket 536. In those embodiments having heated air or cooled air circulated through blanket 536, perforations are formed in the surface of blanket 536 facing the patient so that a portion of the heated or cooled air being circulated through blanket 536 is able to escape from blanket 536 through the perforations and convectively heat or cool, as the case may be, the patient.

Bed 534 includes a pendant controller 544 that a patient uses to control heating/cooling unit 538 in a desired manner when pendant controller 544 is not locked out. In some embodiments, pendant controller 544 also is used to control other bed functions, such as articulation, raising, and lowering of the bed deck, and to control room entertainment and communication functions, such as television, radio, and nurse call. Bed 534 includes a footboard 546 having a control panel 548 that is used by a caregiver to control operation of unit 538, to control operation of various bed functions, and to control various entertainment and communication functions. Control panel 548 is also used by the caregiver to lock out one or more functions of pendant controller 544. For example, the caregiver can lock out the ability of pendant controller 544 to operate unit 538.

An ceiling unit or overhead canopy 550 is coupled to a ceiling 552 of hospital room 532 above bed 534 as shown in FIG. 17. Canopy 550 includes various systems that control the environment of room 532. For example, canopy 532 includes an overhead temperature sensor (not shown), an overhead air quality sensor (not shown), an overhead air purifier (not shown), aroma therapy equipment (not shown), motion or proximity sensors 554 for detecting the presence of other people in the hospital room, examination lights 556, reading lights (not shown), and a video screen 558 for displaying one or more preselected images. Such images may include a scene from nature or other restful scenes. Such images may also include images that transition at the appropriate times during a 24-hour period from day images, such as clouds and sun, to night images, such as moon and stars. Images of the patients family may also be displayed on screen 558.

In some embodiments of room 532, the room lights are controlled to dim slowly as the daytime turns to evening. In addition, a recording of evening sounds, such as owls, night birds, crickets, and wind in the trees is played by audio equipment housed in overhead canopy 550. Eventually, the room lights are turned completely off and the night sounds fade away. In other embodiments of room 532, a video screen similar to or larger than video screen 558 is mounted to a room wall, preferably a wall that confronts the foot end of bed 534. In such alternative hospital rooms, television images, internet images, educational information, patient schedule, imagery to promote relaxation, and video conferencing images are selectively displayed on the video screen.

Bed 534, unit 538, and ceiling unit 550 each have their own controllers for monitoring and controlling the various functions associated with these devices. Each of such controllers include, for example, one or more microprocessors, microcontrollers, memory circuitry, input/output circuitry, signal conditioning circuitry, signal conversion circuitry, power conditioning circuitry, and the like. It is within the scope of this disclosure for each of the controllers of bed 534, unit 538, and canopy 550 to be coupled to the hospital computer network to exchange data with the network. In some embodiments, parameters for controlling bed 534, unit 538, and canopy 550 are entered by computers that are located remotely from room 532. Thus, for example, if a patient places a nurse call requesting the heating/cooling function of unit 538 and blanket 536 be adjusted or discontinued, the nurse receiving the call is able to adjust the amount of heating/cooling provided to the patient via blanket 536.

Figure 18:
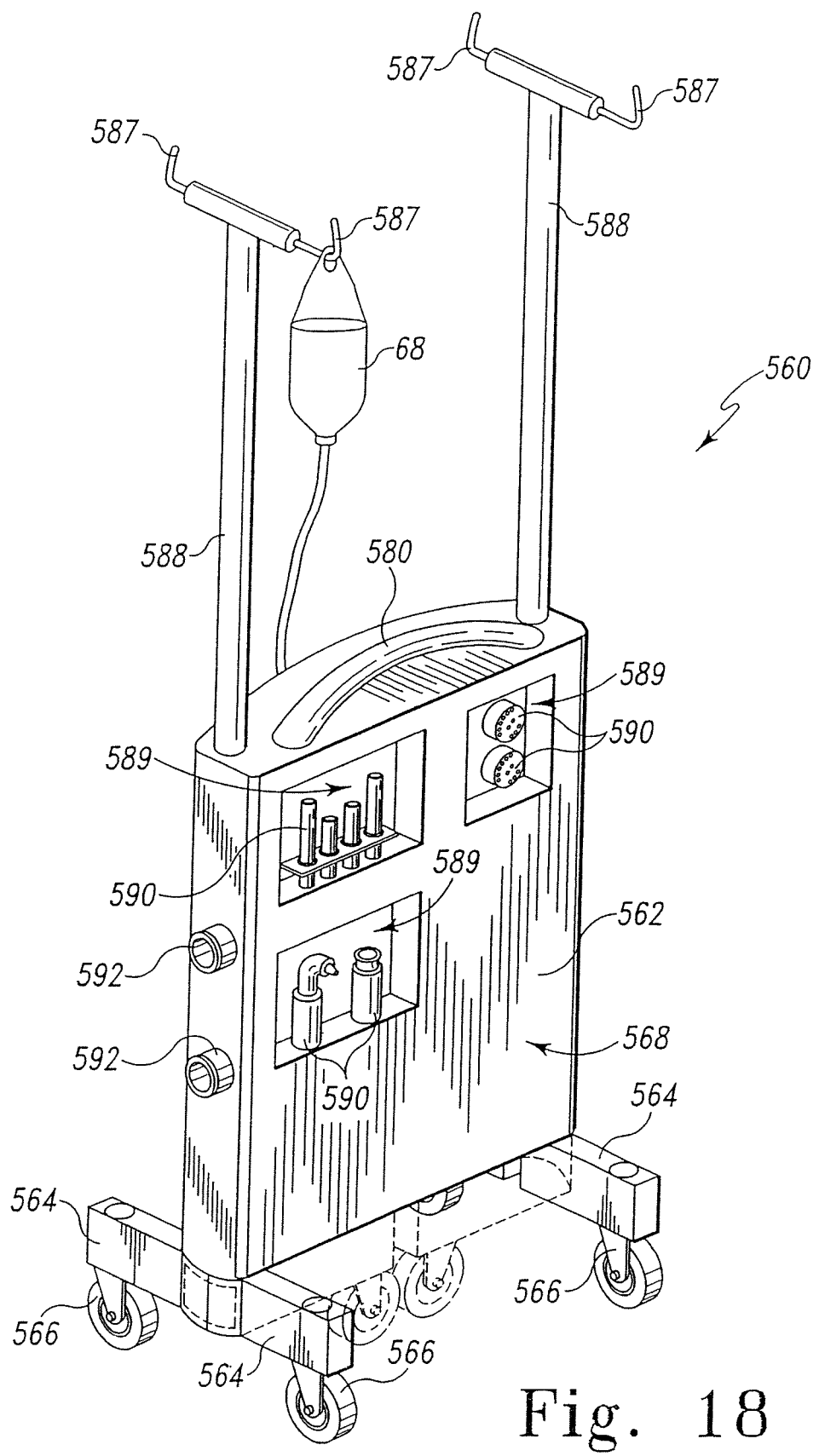
FIG. 18 is a perspective view of a mobile cart according to this disclosure showing the mobile cart having a somewhat rectangular upstanding pedestal, the pedestal having a fairly small depth dimension between a front face and a rear face of the pedestal, the mobile cart having four horizontally extending support legs coupled to the bottom of the pedestal, a set of casters coupled to distal ends of the support legs, and each support leg being pivotable relative to the pedestal about a respective vertical axis between a first position (in solid) extending outwardly from beneath the pedestal and a second position (in phantom) tucked beneath the pedestal.
Figure 19:
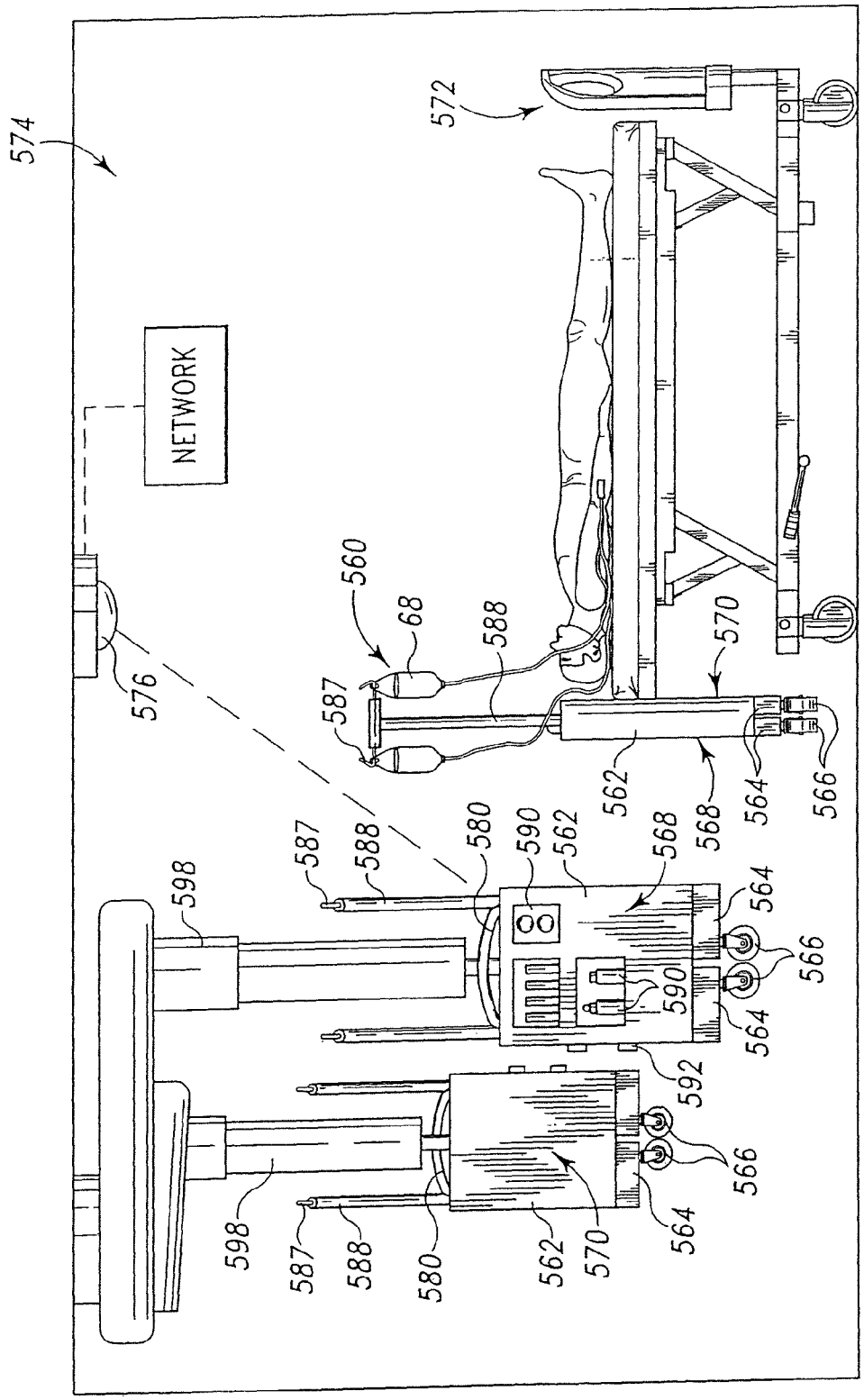
FIG. 19 is a side plan view of a first hospital room showing the mobile cart of FIG. 18 being mounted to a head end of a hospital bed, a second mobile cart, like the mobile cart of FIG. 18, being suspended from a ceiling of the room by an arm assembly, the support legs of the two mobile carts all being in their respective second positions, and the casters of the two mobile carts all being spaced apart from a floor of the room.
Figure 20:
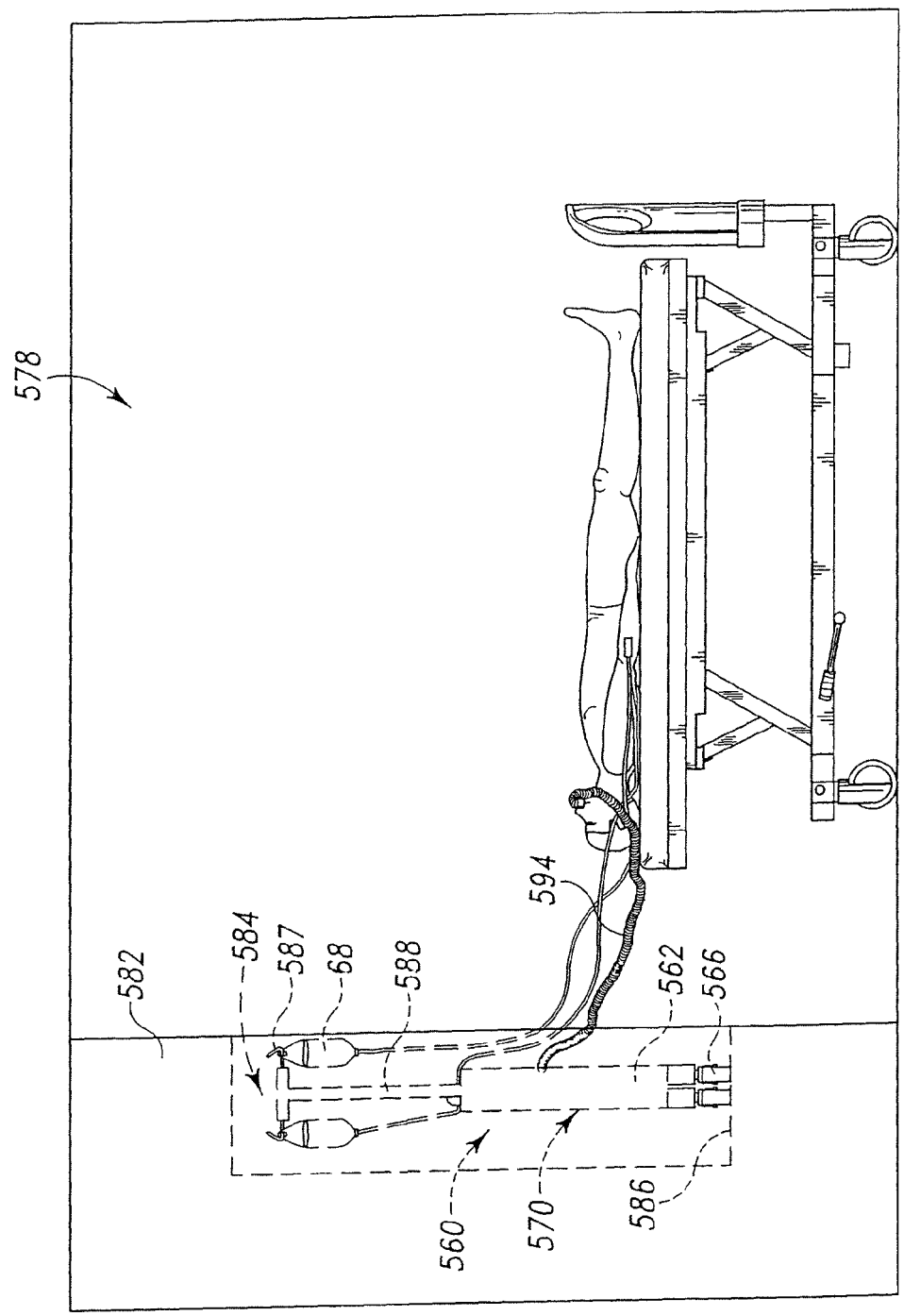
FIG. 20 is side plan view of a second hospital room showing the mobile cart (in phantom) being situated in a cavity (in phantom) formed in a headwall of the hospital room.

Referring now to FIGS. 18-20, a mobile cart 560 includes a somewhat rectangular upstanding pedestal 562, four horizontally extending support legs 564 coupled to the bottom of pedestal 562, and a set of wheels or casters 566 coupled to distal ends of corresponding support legs 564. Pedestal 562 has a fairly small depth dimension between a front face 568 thereof, shown best in FIG. 18, and a rear face 570 thereof, shown in FIGS. 19 and 20. Each support leg 564 is pivotable relative to pedestal 562 about a respective vertical axis between a first position extending outwardly from beneath pedestal 562 as shown in FIG. 18 and a second position tucked beneath pedestal 562 as shown in FIGS. 18-20.

When legs 564 are in the second positions, legs 564 and casters 566 are positioned to lie completely under and within the foot print of pedestal 562. In addition, when legs 564 are in the second positions, legs 564 extend in substantially parallel relation with front and rear faces 568, 570 of pedestal 562. When legs 564 are in the first positions, a majority of legs 564 are positioned to lie outside the foot print of pedestal 562 and legs 564 extend in substantially perpendicular relation to front and rear faces 568, 570 of pedestal 562. Suitable locking or retention mechanisms are provided either on legs 564 or pedestal 562 to lock or retain legs 564 in the respective first and second positions. The stability of cart 560 on a floor is greater when legs 564 are in the first positions than when legs 564 are in their second positions.

Mobile cart 560 is couplable to and transportable with a wheeled hospital bed or stretcher 572 from an operating room 574, shown in FIG. 19, to an intensive care unit room (not shown), and then to a regular hospital room 578, shown in FIG. 20. Of course, rooms 574, 578 are shown merely as examples of hospital rooms and therefore, cart 560 may be transported with stretcher 572 to any location in a hospital that stretcher 572 is capable of going. Cart 560 may also be transported by itself throughout a hospital when legs 564 are in their first positions having casters 566 rolling along the floor of the hospital.

An asset tracking system (not shown) included in a hospital includes a plurality of transmitters, receivers, and/or transmitter/receiver units 576 (collectively referred to as "transmitter/receiver units 576") located throughout the hospital. One such transmitter/receiver unit 576 is shown in FIG. 36. Transmitter/receiver units 576 cooperate with remote equipment, such as computers, included in the asset tracking system to track the whereabouts of mobile carts 560 throughout the hospital. Thus, each cart 560 to be tracked includes a transmitter/receiver unit (not shown) that, when prompted by a signal from transmitter/receiver units 576, emits a signal that is sensed by one or more transmitter/receiver units 576 in the vicinity thereof.

Cart 560 is couplable to hospital bed 572 as previously mentioned. Cart 560 is also couplable to min assemblies 598 included, for example, in operating room 574 and in intensive care unit rooms (not shown). Arm assemblies 598 extend from the ceilings of the respective rooms, such as room 574 as shown in FIG. 19. When cart 560 is coupled to arm assemblies 578, cart 560 is suspended from the ceiling of the respective room so that casters 566 of cart 560 are spaced apart from the floor of the respective rooms. Casters 566 are also spaced apart from the floor of the respective rooms when cart 560 is coupled to bed 572. It is within the scope of this disclosure for cart 560 to be coupled to or included in columns 40, 42 of any of architectural systems 30, 230, 330, as well as any alternatives of these, described above with regard to FIGS. 1-16.

Cart 560 includes suitable couplers (not shown) that interface with couplers (not shown) included in bed 572, with couplers (not shown) included in arm assemblies 578, and with couplers (not shown) included in columns 40, 42. Suitable couplers may include, for example, hooks, clips, posts, latches, sockets, rails, channels, slots, bands, straps, fingers, flanges, lugs, bails, wires, magnets, plates, and the like, as well as combinations of these. Cart 560 includes a handle 580 appended to the top of pedestal 562 as shown in FIGS. 18 and 19. A caregiver grips handle 580 to maneuver cart 560 along a floor of the hospital and to carry cart 560, such as during attachment to or detachment from bed 572, arm assemblies 578, or columns 40, 42.

A headwall 582 of room 578 is formed to include a cavity 584 that is configured to receive cart 560 as shown in FIG. 20. In addition, cart 560 is received in cavities 34, 36 (or cavities 23, 236) when cart 560 is coupled to or included in columns 40, 42 and columns 40, 42 are moved to the storage positions. When cart 560 is situated in cavity 584, legs 564 are in the respective second positions and casters 566 rest upon a ledge surface 586 that underlies cavity 584. Pedestal 562 of cart 560 is configured to carry one or more IV poles 588 as shown in FIGS. 18-20. Cavity 584 has sufficient height to accommodate cart 560 and any IV poles 588 coupled thereto as shown in FIG. 20. Hooks 587 are provided at the top of IV poles 588 for attachment of IV bags 68.

Pedestal 562 includes recesses or compartments 589 that are adapted to carry various patient-monitoring and patient-care modules or equipment 590, shown best in FIG. 18. Such patient-care equipment includes, for example, infusion pumps, ventilator control units, gas control units, vital signs monitors, and the like. Some modules 590 are coupled to the patient, via sensor lines, to monitor various physiological conditions and vital signs of the patient. In some embodiments, cart 560 includes an on-board computer system that interfaces with modules 590 and with a receiver/transmitter unit on cart 560. In such embodiments, patient-data from modules 590 is either transmitted to the hospital network via the receiver/transmitter unit or the patient-data is stored in the computer system until a hard-wire or optical connection is made to the network. When the computer system is communicatively coupled to the network, a caregiver located in the hospital remote from cart 560 is able to access the network with a remote computer terminal, for example, to obtain the status of the patient being monitored by modules 590 carried by cart 560. Cart 560 includes a battery (not shown) to provide power to any electrical components, such as modules 590 and the computer system, carried by cart 560.

Pedestal 562 is formed to include service delivery ports 592. Tanks (not shown) containing oxygen or other types of medical gases are situated in an interior region of pedestal 562. In some embodiments, such tanks are included in a ventilator system carried by cart 560. In such embodiments, hoses 594, one of which is shown in FIG. 20, are coupled to respective ports 592 and extend from ports 592 either to the patient or to associated medical equipment. Cart 560 is configured to carry other types of medical devices, including drug infusion devices, that are associated with providing intensive care to a patient. Such devices are sometimes referred to as LSTAT (Life Support for Trauma and Transport) devices. Because cart 560 carries most, if not all, of the medical equipment necessary to provide intensive care to the patient and because cart 560 is transported with the patient throughout the hospital, the need to disconnect and reconnect IV lines, ventilator hoses, sensor lines, and the like from the patient before and after transport is avoided, as is the need to manage multiple wheeled stands or carts during transport of the patient throughout a hospital.

Figure 21:
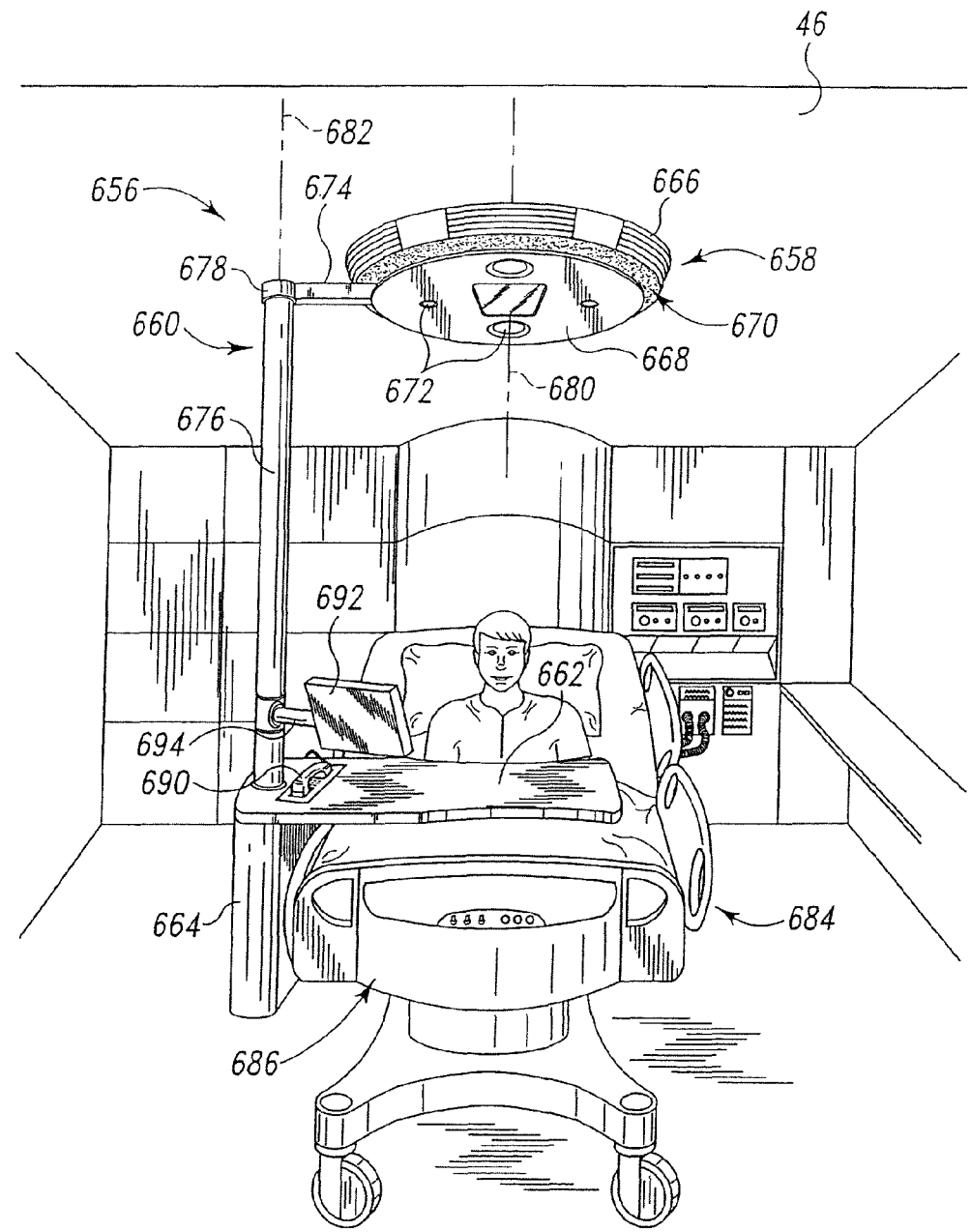
FIG. 21 is a perspective view of a hospital bed supported on a floor of a hospital room and an overbed table assembly that is suspended from a ceiling of a hospital room showing the overbed table assembly including a hub unit coupled to the ceiling above the hospital bed, an arm assembly coupled to the hub unit and extending downwardly therefrom, an entertainment-and-control panel coupled to a vertical arm of the arm assembly, an overbed table coupled to the vertical arm beneath the entertainment-and-control panel, and a telephone coupled to the overbed table.
Figure 23:
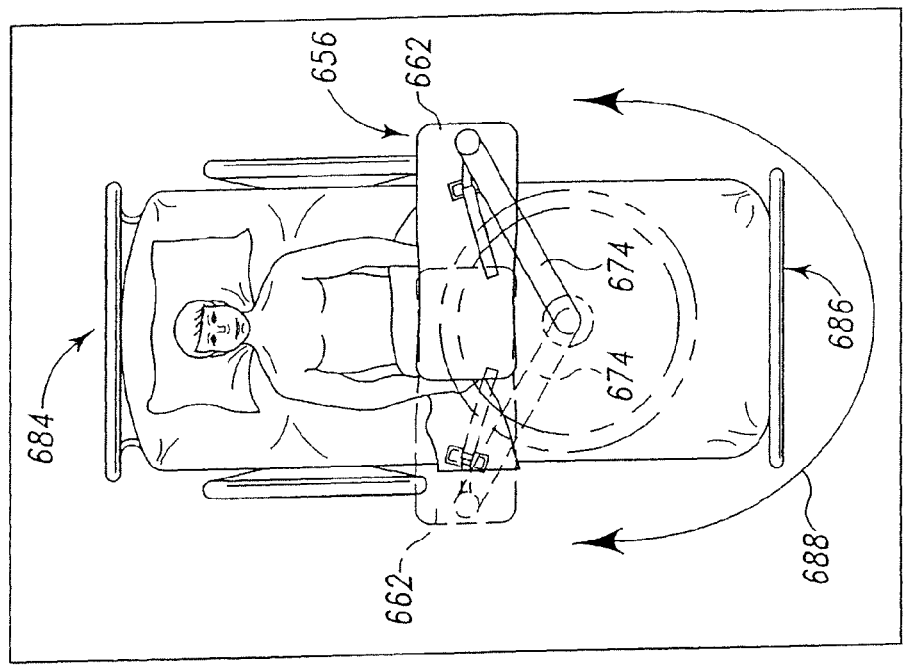
FIG. 23 is a top plan view of the hospital bed and the overbed table assembly of FIG. 22 showing the arm assembly moving between a first position (in solid) having the overbed table extending over a lap of the patient from a first side of the hospital bed and a second position (in phantom) having the overbed table extending over the lap of the patient from a second side of the bed and showing that the service-delivery housing moves around a foot end of the bed as the arm assembly moves between the first and second positions.
Figure 22:
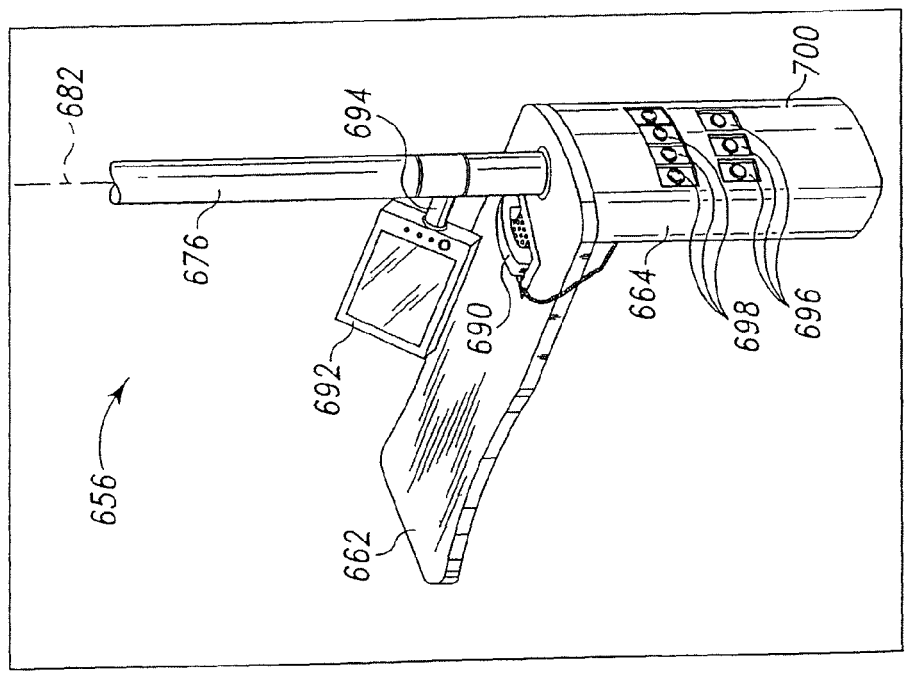
FIG. 22 is a perspective view of a portion of the overbed table assembly of FIG. 21 showing the overbed table assembly including a service-delivery housing coupled to an underside of the overbed table and a plurality of medical service outlets on an end face of the service-delivery housing.

Referring now to FIGS. 21-23, a ceiling-mounted overbed table assembly 656 includes a ceiling unit or hub unit 658 coupled to ceiling 46 of a hospital room, an arm assembly 660 coupled to hub unit 658, an overbed table 662 coupled to arm assembly 660, and a patient-care housing 664 coupled to and extending downwardly from an undersurface of table 662. In alternative embodiments, housing 664 is coupled to arm assembly 660 and is situated, at least in part, beneath table 662. Hub unit 658 includes an annular upper portion 666 having a frustoconical shape, an annular lower portion 668 shaped like a disc, and an annular slot 670 defined between portions 666, 668 as shown in FIG. 40. Hub unit 658 further includes a plurality of exam and reading lights 672 coupled to lower portion 668 and arranged to direct light downwardly therefrom. In alternative embodiments, hub 568 has shapes other than annular, such as elliptical, polygonal (i.e., square, rectangular, triangular, and so on), and the like.

Arm assembly 660 includes a first arm 674 extending horizontally from slot 670 and a second arm 676 extending vertically downwardly from a distal end 678 of first arm 674 as shown in FIG. 21. Hub unit 658 includes a shaft assembly (not shown) that interconnects portions 666, 668 of hub unit 658. A proximal end (not shown) of first arm 674 is coupled to the shaft assembly for pivoting movement about a vertical axis 680. Table 662 and housing 664 are coupled to a lower end of arm 676 for pivoting movement about a vertical axis 682, shown in FIGS. 21 and 22. Alternatively, table 662 and housing 664 are fixed with respect to arm 676 and arm 676 is coupled to arm 674 for rotation about axis 682.

Second arm 676, table 662, and housing 664 are movable between a first position situated on a first side of a hospital bed 684 and a second position situated on a second side of hospital bed 684 as shown in FIG. 23. During movement between the first and second positions, arm 676, table 662, and housing 664 move along an arcuate path, indicated by a curved double-headed arrow 688 shown in FIG. 23, around a foot end 686 of bed 684. First arm 674 has sufficient length to allow housing 664 to clear foot end of bed 684 during movement between the first and second positions. Assembly 656 includes suitable locking mechanisms to lock arm assembly 660 and table 662 in the first and second positions. When in either the first position or the second position, table 662 extends horizontally from arm 676 in a cantilevered manner and is positioned, in part, over the lap of a patient supported by bed 684. In some embodiments, assembly 656 includes drive mechanisms that operate to adjust the vertical position of table 662 and housing 664 relative to arm 676.

Assembly 656 includes a telephone 690 having a handset that resides in a recess formed in the upper surface of table 662. Assembly 656 also includes an entertainment-and-control panel 692 that is coupled to arm 676 of arm assembly 660 via a post 694 that extends horizontally away from arm 676 above table 662 as shown in FIGS. 21 and 22. Illustrative panel 692 is a touch screen that permits the patient to control, for example, room lighting, room temperature, television functions, nurse call functions, and the like. Panel 692 is also operable to display various images such as, for example, television images, internet images, educational information, patient schedule, patient billing information, and video conferencing images. Controls panels having any combination of the above-mentioned control functions and entertainment functions are within the scope of this disclosure. Telephone 690 is used in a conventional manner for placement of phone calls.

A plurality of medical service outlets 696 and a plurality of patient-monitor modules 698 are coupled to an end face 700 of housing 664 as shown in FIG. 22. Modules 698 are arranged in side-by-side relation along an upper portion of end face 700 and medical service outlets 696 are arranged in side-by-side relation beneath modules 698. Each of modules 698 receive patient-data signals via patient-data lines (not shown) that are coupled to modules 698 and to the patient to monitor various physiological conditions of the patient. Patient conditions to be monitored may include temperature, heart rate, blood oxygenation, respiration, brain activity, and the like. Services provided by outlets 696 may include, for example, medical gases, vacuum, and power. Outlets 696 receive the associated services via lines (not shown) that are routed to outlets 696 from the ceiling of the hospital room, through hub unit 658, though interior regions of arms 674, 676, through an opening in table 662, and into an interior region of housing 664. Outlets 696 and modules 698 are positioned on housing 664 so as to be generally inaccessible to a patient lying on bed 684 when assembly 656 is in either the first position or the second position.

It is contemplated by this disclosure that table 662 and/or housing 664, along with outlets 696 and modules 698 associated with housing 664 may be suspended from a ceiling of a hospital room by other types of arm assemblies or columns. For example, it is within the scope of this disclosure for table 662 and/or housing 664 to be coupled to or included in columns 40, 42 of any of architectural systems 30, 230, 330 described above. In such embodiments, table 662 or a part thereof flips up, such as by pivoting about a horizontal axis, thereby placing table 662 is in a substantially vertical orientation for storage in the associated cavity 34, 36, 234, 236 of the associated headwall unit 32, 232. When the column 40, 42 associated with table 662 is moved out of the associated cavity 34, 36, 234, 236, table 662 is flipped down to a substantially horizontal orientation for use.

Although various apparatus and systems have been described in detail with reference to certain preferred embodiments, variations and modifications of each of these apparatus and systems exist within the scope and spirit of the invention as described and defined in the following claims.

The invention claimed is:

1. A hospital equipment system comprising
   a head wall of a room,
   a blanket,
   a thermoregulation unit housed in the head wall, and
   at least one hose coupled to the blanket and coupled to the thermoregulation unit, a medium being moved between the blanket and the thermoregulation unit through the at least one hose, the medium being one of cool liquid, cool air, heated liquid, and heated air, and
   a hospital bed spaced from the head wall, the bed including a pendant controller that a patient uses while lying in bed to control the thermoregulation unit in a desired manner when the pendant controller is not locked out, wherein the pendant controller also is used to control other bed functions, the thermoregulation unit also being controllable by a computer located remotely from said room in which the head wall, the blanket, the thermoregulation unit, and the hospital bed are situated.

2. The set of hospital equipment of claim 1, wherein the blanket comprises a disposable heating/cooling blanket.

3. The set of hospital equipment of claim 1, wherein the at least one hose comprises a pair of heating/cooling hoses and the thermoregulation unit comprises a heating/cooling unit.

4. The set of hospital equipment of claim 3, wherein the medium comprises a cooling medium and when the patient is to be cooled, the heating/cooling unit operates to provide the cooling medium through a first heating/cooling hose of the pair of heating/cooling hoses to the blanket and a second heating/cooling hose of the pair of heating/cooling hoses provides the cooling medium back to heating/cooling unit after circulation of the cooling medium through blanket.

5. The set of hospital equipment of claim 3, wherein the medium comprises a heating medium and when the patient is to be heated, the heating/cooling unit operates to provide the heating medium through a first heating/cooling hose of the pair of heating/cooling hoses to the blanket and a second heating/cooling hose of the pair of heating/cooling hoses provides the heating medium back to heating/cooling unit after circulation of the cooling medium through blanket.

6. The set of hospital equipment of claim 1, wherein the medium comprises heated air circulated through the blanket and wherein perforations are formed in a surface of the blanket facing the patient so that a portion of the heated air being circulated through the blanket is able to escape from the blanket through the perforations and convectively heat the patient.

7. The set of hospital equipment of claim 1, wherein the medium comprises cooled air circulated through the blanket and wherein perforations are formed in a surface of the blanket facing the patient so that a portion of the cooled air being circulated through the blanket is able to escape from the blanket through the perforations and convectively cool the patient.

8. The set of hospital equipment of claim 1, wherein the other bed functions comprise at least one of articulation, raising, and lowering of a deck of the bed.

9. The set of hospital equipment of claim 1, wherein the other bed functions comprise at least one of control of a room entertainment function and control of a communication function.

10. The set of hospital equipment of claim 1, wherein the other bed functions comprise at least one of control of a television, control of a radio, and placing a nurse call.

11. The set of hospital equipment of claim 1, wherein the thermoregulation unit is operable to selectively move each of cool liquid, cool air, heated liquid, and heated air between the blanket and the thermoregulation unit through the hose.

12. A hospital equipment system comprising
    a head wall of a room,
    a blanket,
    a thermoregulation unit housed in the head wall,
    at least one hose coupled to the blanket and coupled to the thermoregulation unit, a medium being moved between the blanket and the thermoregulation unit through the at least one hose, the medium being one of cool liquid, cool air, heated liquid, and heated air, and
    a hospital bed spaced from the head wall, the bed including a footboard having a control panel that is used by a caregiver to control operation of the thermoregulation unit, wherein the control panel is also used by a caregiver to control operation of other bed functions, the thermoregulation unit also being controllable by a computer located remotely from said room in which the head wall, the blanket, the thermoregulation unit, and the hospital bed are situated.

13. The set of hospital equipment of claim 12, wherein the other bed functions comprise at least one of an entertainment function and a communication function.

14. The set of hospital equipment of claim 12, wherein the bed includes a pendant controller that a patient uses to control the thermoregulation unit in a desired manner when the pendant controller is not locked out and wherein the control panel is also used by the caregiver to lock out one or more functions of the pendant controller.

15. The set of hospital equipment of claim 12, wherein the thermoregulation unit is operable to selectively move each of cool liquid, cool air, heated liquid, and heated air between the blanket and the thermoregulation unit through the hose.

16. A hospital equipment system comprising
    a head wall of a room,
    a blanket,
    a thermoregulation unit housed in the head wall,
    at least one hose coupled to the blanket and coupled to the thermoregulation unit, a medium being moved between the blanket and the thermoregulation unit through the at least one hose, the medium being one of cool liquid, cool air, heated liquid, and heated air, and
    a hospital bed spaced from the head wall, the bed including a footboard having a control panel that is used by a caregiver to control operation of the thermoregulation unit, wherein the bed includes a pendant controller that a patient uses to control the thermoregulation unit in a desired manner when the pendant controller is not locked out and wherein the control panel is also used by the caregiver to lock out the ability of the pendant controller to operate the thermoregulation unit, the thermoregulation unit also being controllable by a computer located remotely from said room in which the head wall, the blanket, the thermoregulation unit, and the hospital bed are situated.

17. The set of hospital equipment of claim 16, wherein the thermoregulation unit is operable to selectively move each of cool liquid, cool air, heated liquid, and heated air between the blanket and the thermoregulation unit through the hose.

\* \* \* \* \*